United States Patent
Szendrei-Temesi et al.

(10) Patent No.: US 10,488,335 B2
(45) Date of Patent: Nov. 26, 2019

(54) GAS AND VAPOR SENSING DEVICES BASED ON 2D NANOSHEET MATERIAL

(71) Applicant: MAX-PLANCK-GESELLSCHAFT ZUR FÖRDERUNG DER WISSENSCHAFTEN E.V., Munich (DE)

(72) Inventors: Katalin Szendrei-Temesi, München (DE); Pirmin Ganter, Stuttgart (DE); Olalla Sanchez-Sobrado, Stuttgart (DE); Alexander Hunger, Leipzig (DE); Bettina Lotsch, Pahl (DE)

(73) Assignee: MAX-PLANCK-GESELLSCHAFT ZUR FÖRDERUNG DER WISSENSCHAFTEN E.V. (DE)

( * ) Notice: Subject to any disclaimer, the term of this patent is extended or adjusted under 35 U.S.C. 154(b) by 167 days.

(21) Appl. No.: 15/538,493

(22) PCT Filed: Nov. 26, 2015

(86) PCT No.: PCT/EP2015/077807
§ 371 (c)(1),
(2) Date: Jun. 21, 2017

(87) PCT Pub. No.: WO2016/102139
PCT Pub. Date: Jun. 30, 2016

(65) Prior Publication Data
US 2017/0350816 A1 Dec. 7, 2017

(30) Foreign Application Priority Data

Dec. 23, 2014 (EP) .................................... 14200196
Feb. 18, 2015 (EP) .................................... 15155532

(51) Int. Cl.
*G01N 1/22* (2006.01)
*G01N 31/00* (2006.01)
(Continued)

(52) U.S. Cl.
CPC .......... *G01N 21/45* (2013.01); *G01N 27/4071* (2013.01); *G01N 27/4074* (2013.01)

(58) Field of Classification Search
CPC ...... G01N 1/22; G01N 31/00; G01N 27/4071; G01N 21/45; G01N 27/4074
(Continued)

(56) References Cited

U.S. PATENT DOCUMENTS 7,948,478 B2     5/2011 Chuang
2014/0207467 A1  7/2014 White et al.
(Continued)

FOREIGN PATENT DOCUMENTS

EP    2752466 A2   7/2014
FR    2577207 A1   8/1986
(Continued)

OTHER PUBLICATIONS

B. V. Lotsch, F. Scotognella, K. Moeller, T. Bein and G. A. Ozin, Proc. SPIE , 2010, 7713V.
(Continued)

*Primary Examiner* — Brian J. Sines

(57) ABSTRACT

The present invention relates to a device, comprising at least one layer of an active material having a first optical thickness, the active material being selected so as to experience a change (i) of at least one size dimension, (ii) of the resistance, (iii) of the refractive index or (iv) combinations of two or more of the foregoing, when the active material is subjected to a change in environment, wherein at least one and preferably all of the layers of the at least one layer of the active material is composed of at least two nanosheets of the active material, with the at least two nanosheets randomly overlapping one another. The invention further relates to a nanosheet of active material and to a use of the nanosheet of the material.

22 Claims, 6 Drawing Sheets

Figure 1:
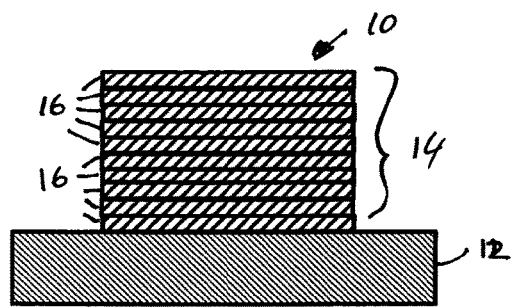

(51) Int. Cl.
*G01N 21/45* (2006.01)
*G01N 27/407* (2006.01)

(58) Field of Classification Search
USPC ..... 422/50, 400, 421, 82.05, 83, 85; 436/43, 436/164
See application file for complete search history.

(56) References Cited

U.S. PATENT DOCUMENTS

| 2014/0242389 | A1* | 8/2014 | Mahler | H01L 21/02601 |
| --- | --- | --- | --- | --- |
| | | | | 428/403 |
| 2014/0287237 | A1* | 9/2014 | Mahler | B82Y 15/00 |
| | | | | 428/403 |
| 2015/0069295 | A1* | 3/2015 | Ho | B01J 37/036 |
| | | | | 252/188.25 |
| 2017/0044683 | A1* | 2/2017 | Cullen | C01B 25/00 |

FOREIGN PATENT DOCUMENTS

| JP | 3321601 | B2 | 9/2002 |
| --- | --- | --- | --- |
| WO | 2011044682 | A1 | 4/2011 |
| WO | 03021302 | A2 | 3/2013 |
| WO | 2013130140 | A1 | 9/2013 |
| WO | 2013164255 | A1 | 11/2013 |

OTHER PUBLICATIONS

Bonifacio, L. D. et al. Towards the Photonic Nose: A Novel Platform for Molecule and Bacteria Identification. Advanced Materials 22, 1351-1354, doi:10.1002/adma.200902763 (2010).
Borini, S. et al. Ultrafast Graphene Oxide Humidity Sensors. ACS Nano 7, 11166-11173, doi:10.1021/nn404889b (2013).
Calvo, M. E., Sánchez-Sobrado, O., Colodrero, S. & Miguez, H. Control over the Structural and Optical Features of Nanoparticle-Based One-Dimensional Photonic Crystals. Langmuir 25, 2443-2448, doi:10.1021/la8030057 (2009).
Camerel, F., Gabriel, J. C. P., Batail, P., Panine, P. & Davidson, P. Combined SAXS-Rheological Studies of Liquid-Crystalline Colloidal Dispersions of Mineral Particles. Langmuir 19, 10028-10035, doi:10.1021/la034626p (2003).
Chen, S., Wang, Y., Choi, S. Applications and Technology of Electronic Nose for Clinical Diagnosis. Open Journal of Applied Biosensor 2, 39-50, doi:10.4236/ojab.2013.22005 (2013).
Colodrero, S., Ocaña, M., González-Elipe, A. R. & Míguez, H. Response of Nanoparticle-Based One-Dimensional Photonic Crystals to Ambient Vapour Pressure. Langmuir 24, 9135-9139, doi:10.1021/la801210q (2008).
Decaillon, J. G., Andres, Y., Abbe, J. C. & Tournoux, M. M+/H+ ion exchange behavior of the phosphoantimonic acids $HnSbnP2O3n+5 \cdot xH2O$ (n=1,3) for M=Cs and other alkali metal ions. Solid State Ionics 112, 143-152, doi:10.1016/S0167-2738(98)00227-6 (1998).
Deniard-Courant, S., Pittard, Y., Barboux, P. & Livage, J. Relative humidity influence on the water content and on the protonic conductivity of the phosphoantimonic acids $HnSbnP2O3n+5 \cdot xH2O$ (n=1, 3, 5). Solid State Ionics 27, 189-194, doi:10.1016/0167-2738(88)90009-4 (1988).
England, W. A., Cross, M. G., Hamnett, A., Wiseman, P. J. & Goodenough, J. B. Fast proton conduction in inorganic ion-exchange compounds. Solid State Ionics 1, 231-249, doi:10.1016/0167-2738(80)90007-7 (1980).
European Search Report for related European Application No. EP15155532,3; dated Mar. 4, 2016; 3 pages.
Exner, A. T. et al. A step towards the electrophotonic nose: integrating 1D photonic crystals with organic light-emitting diodes and photodetectors. Laser & Photonics Reviews, n/a-n/a, doi:10.1002/lpor.201300220 (2014).
Fenzl, C., Hirsch, T. & Wolfbeis, O. S. Photonic Crystals for Chemical Sensing and Biosensing. Angewandte Chemie International Edition 53; 3318-3335; doi:10.1002/anie.201307828 (2014).

Fuertes, M. C. et al. Sorption Properties of Mesoporous Multilayer Thin Films. The Journal of Physical Chemistry C 112, 3157-3163, doi:10.1021/jp710612y (2008).
Gallegos, D. et al. Label-free biodetection using a smartphone. Lab on a Chip 13, 2124-2132, doi:10.1039/C3LC40991K (2013).
Ghazzal, M. N., Deparis, O., De Coninck, J. & Gaigneaux, E. M. Tailored refractive index of inorganic mesoporous mixed-oxide Bragg stacks with bio-inspired hygrochromic optical properties. Journal of Materials Chemistry C 1, 6202-6209, doi:10.1039/C3TC31178C (2013).
Greenspan, L. Humidity Fixed Points of Binary Saturated Aqueous Solutions. Journal of Research of the National Bureau of Standards, Section A: Physics and Chemistry 81A, 89-96 (1977).
Griffith, C. S., Luca, V., Cochrane, J. & Hanna, J. V. Lanthanide/actinide ion-exchange and structural investigations of the layered phosphatoantimonic acid, $H3Sb3P2O14 \cdot ZH2O$. Microporous Mesoporous Mater. 111, 387-403, doi:10.1016/j.micromeso.2007.08.028 (2008).
Han, J., Don, Y., Wei, M., Evans, D. G. & Duan, X. Tunable/switchable one-dimensional photonic crystals based on a multilayer architecture of layered double hydroxides and titanium dioxide. RSC Advances 2, 10488-10491, doi:10.1039/C2RA20790G (2012).
Hidalgo, N., Calvo, M. E. & Míguez, H. Mesostructured Thin Films as Responsive Optical Coatings of Photonic Crystals. Small 5, 2309-2315, doi:10.1002/smll.200900411 (2009).
Hinterholzinger, F. M. et al. One-dimensional metal-organic framework photonic crystals used as platforms for vapour sorption. Journal of Materials Chemistry 22, 10356-10362, doi:10.1039/C2JM15685G (2012).
Holtz, J. H. & Asher, S. A. Polymerized colloidal crystal hydrogel films as intelligent chemical sensing materials. Nature 389, 829-832 (1997).
International Preliminary Report on Patentability for International Application No. PCT/EP2015/077807; dated Dec. 23, 2014; 9 pages.
International Search Report for International Application No. PCT/EP2015/077807; dated Dec. 23, 2014; 4 pages.
J. D. Joannopoulos, S. G. J., J. N. Winn, R. D. Meade. Photonic Crystals Molding the flow of light. Princeton University press 2nd edition, 4 (2008).
Jamil, H. et al. Electrospun titanium dioxide nanofiber humidity sensors with high sensitivity. Ceramics International 38, 2437-2441, doi:http://dx.doi.org/10.1016/j.ceramint.2011.11.010 (2012).
Jean-Christophe P. Gabriel et al: Swollen liquid-crystalline lamellar phase based on extended solid-like sheets, Nature, vol. 413, Oct. 4, 2001 (Oct. 4, 2001), pp. 504-508, XP055253252, DOI: 10.1038/35097046.
Jun Feng et al: "Giant Moisture Responsiveness of VS 2 Ultrathin Nanosheets for Novel Touchless Positioning Interface", Advanced Materials, vol. 24, No. 15, Apr. 17, 2012 (Apr. 17, 2012), pp. 1969-1974 XP055252879, DE ISSN: 0935-9648, DOI: 10.1002/adma.201104681.
Kobler, J., Lotsch, B. V., Ozin, G. A. & Bein, T, Vapour-Sensitive Bragg Mirrors and Optical Isotherms from Mesoporous Nanoparticle Suspensions, ACS Nano 3, 1669-1676, doi:10.1021/nn800911c (2009).
Kuang, Q., Lao, C., Wang, Z. L., Xie, Z. & Zheng, L. High-Sensitivity Humidity Sensor Based on a Single SnO2 Nanowire. Journal of the American Chemical Society 129, 6070-6071, doi:10.1021/ja070788m (2007).
Kuhn, A., Holzmann, T., Nuss, J. & Lotsch, B. V. A facile wet chemistry approach towards unilamellar tin sulfide nanosheets from $Li4xSn1-xS2$ solid solutions. J. Mater. Chem. A, doi:10.1039/C3TA14190J (2014).
Lachgar, A., Deniard-Courant, S. & Piffard, Y. Adsorption and structural studies of water in the layered compounds $K3Sb3M2O14$, $xH2O$ (M=P, As). Journal of Solid State Chemistry 73, 572-576, doi:http://dx.doi.org/10.1016/0022-4596(88)90147-8 (1968).
Lee, D., Omolade, D., Cohen, R. E. & Rubner, M, F. pH-Dependent Structure and Properties of TiO2/SiO2 Nanoparticle Muitilayer Thin Films. Chemistry of Materials 19, 1427-1433, doi:10.1021/cm070111y (2007).

(56) References Cited

OTHER PUBLICATIONS

Lee, Y.-J., Pruzinsky, S. A. & Braun, P. V. Glucose-Sensitive Inverse Opal Hydrogels: Analysis of Optical Diffraction Response. Langmuir 20, 3096-3106, doi:10.1021/la035555x (2004).
Lotsch, B. V. & Ozin, G. A. Clay Bragg Stack Optical Sensors. Advanced Materials 20, 4079-4084, doi:10.1002/adma.200800914 (2008).
Lotsch, B. V. & Ozin, G. A. Photonic Clays: A New Family of Functional 1D Photonic Crystals. ACS Nano 2, 2065-2074, doi:10.1021/nn800375e (2008).
Min Sheng, Leilei Gu, Roman Kontic, Ying Zhou, Kaibo Zheng, Guorong Chen, Xiaoliang Mo, Greta R. Patzke: Humidity sensing properties of bismuth phosphates, Sensors and Actuators B 166-167 (2012), 642-649, doi: 10.1016/j.snb.2012.03.030.
Miura, N., Mizuno, H. & Yamazoe, N. Humidity sensor using antimony phosphate operative at a medium temperature of 150-250°C. Jpn. J. Appl. Phys., Part 2 27, L931-L933 (1988).
Moon, C. S., Kim, H.-R., Auchterlonie, G., Drennan, J. & Lee, J.-H. Highly sensitive and fast responding CO sensor using $SnO_2$ nanosheets. Sensors and Actuators B: Chemical 131, 556-564, doi:http://dx.doi.org/10.1016/j.snb.2007.12.040 (2008).
Pavlichenko, I. et al. Humidity-Enhanced Thermally Tunable $TiO_2$/$SiO_2$ Bragg Stacks. The Journal of Physical Chemistry C 116, 298-305, doi:10.1021/jp208733t (2011).
Pavlichenko, I. et al. Nanomorphology tuning of the thermal response of $TiO_2$/$SiO_2$ Bragg stacks. Canadian Journal of Chemistry 90, 1069-1077, doi:10.1139/v2012-081 (2012).
Piffard, Y., Lachgar, A. & Tournoux, M. Crystal structure of potassium phosphatoantimonate ($K_3Sb_3P_2O_{14}$). J. Solid State Chem. 58, 253-256 (1985).
Piffard, Y., Verbaere, A., Lachgar, A., Deniard-Courant, S. & Tournoux, M. The layered phosphatoantimonic acid $H_3Sb_3P_2O_{14}$.$xH_2O$. Rev. Chim. Miner. 23, 766-775 (1986).
Tsai, F.-S. & Wang, S.-J. Enhanced sensing performance of relative humidity sensors using laterally grown ZnO nanosheets. Sensors and Actuators B: Chemical 193, 280-287, doi:http://dx.doi.org/10.1016/j.snb.2013.11.069 (2014).
Wang, J., Su, M.-Y., Qi, J.-Q. & Chang, L.-Q. Sensitivity and complex impedance of nanometer zirconia thick film humidity sensors. Sensors and Actuators B: Chemical 139, 418-424, doi:http://dx.doi.org/10.1016/j.snb.2009.03.070 (2009).
Wang, Z. et al. Bioinspired Water-Vapour-Responsive Organic/Inorganic Hybrid One-Dimensional Photonic Crystals with Tunable Full-Colour Stop Band. Advanced Functional Materials 20, 3784-3790, doi:10.1002/adfm.201001195 (2010).
Winston, P. W. & Bates, D. H. Saturated Solutions for the Control of Humidity in Biological Research. Ecology 41, 232-237, doi:10.2307/1931961 (1960).
Xuewen Wang, Zuoping Xiong, Zheng Liu, and Ting Zhang, Exfoliation at the Liquid/Air Interface to Assemble Reduced Graphene Oxide Ultrathin Films for a Flexible Noncontact Sensing Device. Adv. Mater. 2015, 27, 1370-1375, DOI: 10.1002/adma.201404069.
Yang, D. & Frindt, R. F. Powder x-ray diffraction of two-dimensional materials. J. Appl. Phys. 79, 2376-2385, doi:10.1063/1.361165 (1996).
Zhang, L. et al. Facile synthesis and ultrahigh ethanol response of hierarchically porous ZnO nanosheets. Sensors and Actuators B: Chemical 161, 209-215, doi:http://dx.doi.org/10.1016/j.snb.2011.10.021 (2012).
Zhang, S.-L., Choi, H.-H., Yue, H.-Y. & Yang, W.-C. Controlled exfoliation of molybdenum disulfide for developing thin film humidity sensor. Current Applied Physics 14, 264-268, doi:http://dx.doi.org/10.1016/j.cap.2013.11.031 (2014).
Zhang, Y. et al. Synthesis and characterization of $TiO_2$ nanotubes for humidity sensing. Applied Surface Science 254, 5545-5547, doi:http//dx.doi.org/10.1016/j.apsusc.2008.02.106 (2008).
English translation of First Office Action regarding related CN App. No. 2015800708272; dated Apr. 25, 2019; 3 pgs.

* cited by examiner

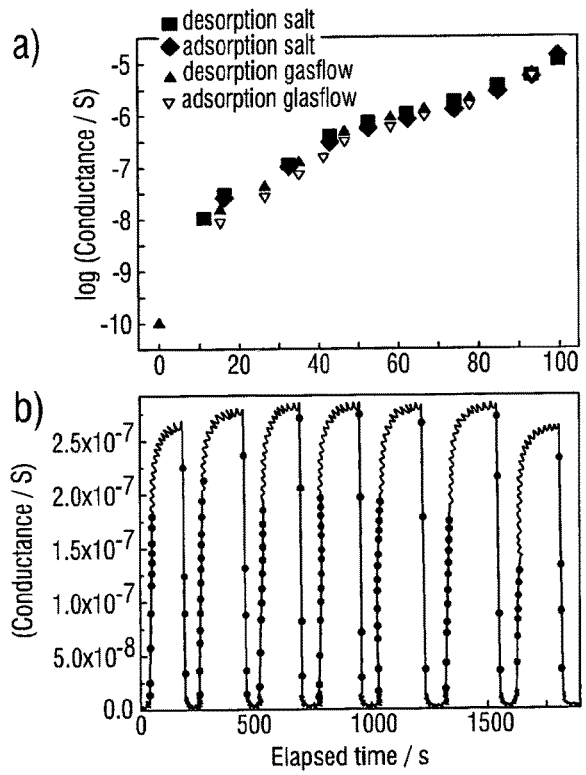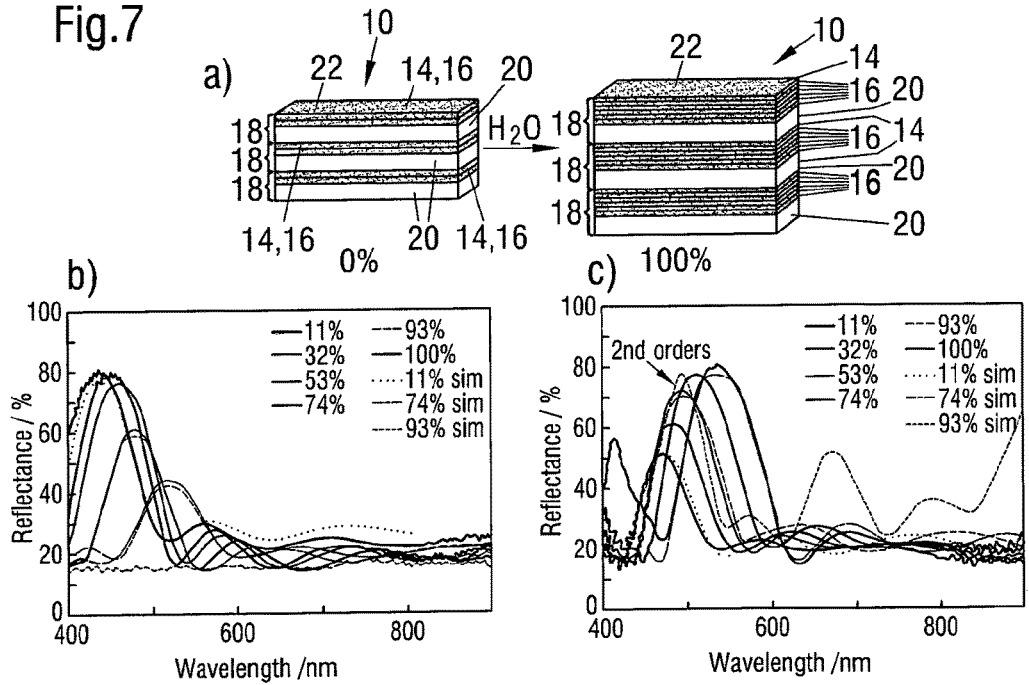

GAS AND VAPOR SENSING DEVICES BASED ON 2D NANOSHEET MATERIAL

CROSS-REFERENCES TO RELATED APPLICATIONS

This patent application is a 371 of International Application No. PCT/EP2015/077807, filed Nov. 26, 2015 which claims the priority of European Application No. 15155532.3, filed Feb. 18, 2015 which claims the priority of European Application No. 14200196.5, filed Dec. 23, 2014 each of which are incorporated herein by reference in their entirety.

The present invention relates to a device, such as a resistive or optical touchless positioning interface, which comprises at least one layer of an active material that is capable of undergoing a change when the active material is subjected to a change in environment, such as a change in humidity of the environment. Moreover, the present invention relates to a nanosheet of active material and to the use of such a nanosheet in particular in a resistive or optical touchless positioning interface.

The exponential growth in digital technology development for a wide variety of electronic devices, such as laptops, smartphones or tablets necessitates the rapid development of novel hardware control systems. In this context, humidity sensors, exhibiting a high spatial sensitivity to the degree of environmental moisture, are promising candidates for use in smart touchless positioning interfaces (TPI) which operate based on local variations in the humid environment, featuring a gradient with a sub centimeter thickness, around the human finger.

However, the existing devices are not satisfactory because they typically exhibit too long response times. Moreover, the spatial sensitivity of these devices is so far not suitable for the implementation in smart touchless positioning interfaces.

For example, zinc oxide (ZnO) is known as an active material, which is a material subject to change in its characteristics in response to a change in the environment. Due to this, it is assumed that this material can be used in electronic sensing devices, such as in humidity sensors or in touchless positioning interfaces. However, ZnO cannot be produced as an ultrathin, planar 2D structure with a sufficiently large surface area on account of its crystallographic structure. For this reason, ZnO is not a suitable material for forming ultrasensitive 2D materials for use in stimuli-responsive devices, such as smartphones and tablets, which require large area displays.

For this reason it is an object of the present invention to provide a device that reacts quickly and with a sufficiently large spatial sensitivity to a change in the environment or atmosphere, such as a change in humidity, and that can be produced in a large area 2D or planar manner cheaply and cost effectively, which therefore can be suitably used in, in particular touchless, sensing applications.

This object is satisfied by a device in accordance with claim 1.

In accordance with the present invention, such a device comprises at least one layer of an active material having a first optical thickness, the active material being selected so as to experience a change (i) of at least one size dimension, (ii) of the resistance, (iii) of the resistivity, (iv) of the refractive index or (v) combinations of two or more of the foregoing, when the active material is subjected to a change in environment, wherein at least one and preferably all of the at least one layer of the active material is composed of at least two nanosheets of the active material, with the at least two nanosheets randomly overlapping one another.

A change in environment is e.g. a change in the level of humidity of the environment and/or a change in the amount of a compound, such as a solid, gas or vapour, which is present in the environment. For example, the compound may be one of the following compounds, namely e.g. ethanol, isopropanol, acetone, other alcohols, amines and solvent vapours or gases such as $CO_2$ in general.

By means of the present invention it is possible to provide devices having a planar 2D structure that can be used in sensing applications, because they are sensitive to changes in the environment which they are subjected to and particularly because they respond with a high sensitivity and within a very short time period to changes in the environment, such as in particular a change in the level of humidity of the environment, i.e. because they have a large sensitivity. More specifically, the devices disclosed herein have a high sensitivity with a response range of over 5 orders of magnitude in resistance, a good cyclability and fast response and recovery times in the range of a few seconds.

As a response to a change in the environment these devices experience a change of (i) of at least one size dimension, (ii) of the resistance, (iii) of the resistivity, (iv) of the refractive index or (v) combinations of two or more of the foregoing.

These devices may be advantageously used for, in particular touchless, positioning interfaces constructed as thin film humidity sensing devices based on phosphatoantimonic acid $Sb_3P_2O_{14}^{3-}$ nanosheets. Due to the aforementioned properties the thin film device can be applied as a touchless positioning interface with a change of ionic conductance between the finger-on and finger-off state by a factor of 170.

In this connection it should be noted that an active material is defined as a material that responds to an external influence. Such an external influence can be a change in humidity or the change in the amount of a compound present in the environment in which the active material is present. That is to say that the active material changes at least some of its properties when subjected to an external stimulus.

In the context of the present invention a layer of active material is composed of at least two nanosheets (also referred to as sheets), with the at least two nanosheets randomly overlapping one another. Moreover, in the most preferred case a nanosheet is a monolayer. The individual nanosheets are thus preferably of atomic or molecular thickness and form a planar sheet made up of the active material. A planar sheet made up of the active material means that the individual atoms of a single sheet are at least substantially all chemically bonded to one another. A chemical bond is either a covalent bond, an ionic bond, or a mixture of covalent and ionic bonds.

Transparent thin films obtained by spin-coating can be applied e.g. as resistive RH (relative humidity) sensors, as the ionic conductance of the film strongly depends on the surrounding RH.

The humidity-responsive photonic device provides the user with a direct optical feedback on a successful interaction such that no additional soft and hardware is required, saving cost, in order to implement the device in applications for contact visualization in current state of the art touch screens. Using e.g. the contact-less optical read-out proposed herein, the disadvantages of conventional touch screens such as scratches or fingerprints can be eliminated, while touchless tracking of finger motion is achieved in a simple fashion without complex electronic circuitry.

The optical tunability, the extremely high sensitivity, reproducibility, fast response and recovery times and the selectivity to e.g. water vapour achieved with these devices, provide a new concept of an optical touchless positioning interface.

In this connection it should be noted that at least one of the nanosheets and preferably all of the nanosheets of the at least one layer of the active material advantageously has/have an average width in the range of 40 nm to 1 mm, preferably between 50 nm and 100,000 nm and an average length in the range of 40 nm to 1 mm and preferably between 50 nm and 100,000 nm. A preferred aspect ratio of the length to width to height of the nanosheets is at least 20:20:1; an aspect ratio of 200:200:1 would be desirable. Such materials can expediently be used in different forms of sensors.

A change in the humidity of the environment e.g. brings about a change of at least one size dimension, and/or of the refractive index, both of which cause a change from the first optical thickness to a second optical thickness. This is because the optical thickness can be defined as the refractive index multiplied by the layer thickness.

In this connection it should be noted that the change in size is typically a change in layer thickness, however, the material experiences virtually no change in one of the lateral (width and length) dimensions.

It should also be noted that a possible further change of one of the physical characteristics of the active material that is measured is generally the resistance of the material. This change can for instance result from a change of the ionic conductivity of the material, which in turn is influenced by the water content.

The change in resistance measured is not necessarily correlated with the other changes of the active material. Nevertheless, when the measured resistance changes, an indication is inherently provided that the humidity level of the environment has changed or that another vapour analyte or gas is present.

Advantageously the change in environment is brought about by a change in humidity of the environment, a change of the presence of a certain gas in the environment and/or a change in the presence of a certain vapour in the environment. This means that the device can be used in different kinds of environments and sense specific changes therein so that it can be used in a wide array of applications. The device can also be selective to more than one component present in the atmosphere. This means that not only a change in the presence of water in the environment but also of certain other compounds, such as ethanol, acetone etc. can be detected.

It is preferred that the active material of at least one and preferably of all of the at least one layer of active material has the general formula:

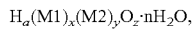

$H_a(M1)_x(M2)_y O_z \cdot nH_2O$, where M1 is selected from the group comprising group 2 elements, group 4 elements, group 5 elements, group 14 elements, group 15 elements, rare earth elements, as well as Mn, Fe, Co, Ni, Zn, Cd and all solid solution and substitution compounds of these elements; M2 is selected from the group of elements comprising group 15 elements, group 5 elements and all solid solutions of these elements, with M2 being different from M1, where a=0-10, preferably a=1 to 5; x=0-10, preferably x=1 to 5, in particular x=1 to 3; y=0-10, preferably y=1 to 10, in particular y=1 to 5, z=1-30, preferably z=1 to 25, in particular z=1 to 10, and n=0-50, preferably n=0 to 20, most preferably n=0 to 10, wherein when x=0, y is not equal to 0, and when y=0, x is not equal to 0.

Such materials can advantageously be provided in the form of nanosheets and typically exhibit the changes required to function in such sensing applications, preferably in touchless sensing applications. The nanosheets constituting the active material according to the present invention are preferably known as or can act as a two dimensional solid acid at standard temperature and pressure.

In accordance with the present invention the term "nanosheet" is defined as a 2D structure that in particular has an aspect ratio of width to length to height of at least 20:20:1, in particular of at least 50:50:1 and preferably of at least 100:100:1.

Advantageously each of the nanosheets has an average sheet thickness of 0.5 to 10 nm, preferably between 0.5 to 3.5 nm, most preferably 0.5 to 2 nm and in particular 1 to 1.4 nm. Such sheet thickness can be determined by AFM (atomic force microscope) measurements or obtained by determining the crystallographic thickness. In order to determine the average sheet thickness an AFM image of the topography of a sheet of the active material is taken (measured in vacuum). As the nanosheets are discrete their thickness can be determined individually for different nanosheets deposited on a substrate and measured along a line across the surface of an individual nanosheet (height profile) or laterally overlapping nanosheets.

It is preferred that at least one and preferably all of the at least one layer of the active material has/have an average layer thickness selected in the range of from 4 nm to 5 mm, preferably 10 nm to 3000 nm, more preferred 15 nm to 2000 nm and in particular 30 nm to 400 nm. These layer thicknesses are chosen such that the apparatus can be used for applications in the UV, the visible and the IR spectral range. The average layer thickness can be measured by cross-sectional scanning electron microscopy or by spectroscopic ellipsometry as well as by AFM.

Such layer thickness can also be termed thin films. Such thin films are typically composed of several randomly overlapping or ordered single nanosheets of the active material and can advantageously be manufactured using a spin coating, dip coating, spray coating, drop casting or electrochemical deposition method. In this connection it should be noted that the term "ordered single nanosheets" refers to the orientational or crystallographic ordering along the nanosheet normal, i.e. in the stacking direction of the thin films.

In some embodiments it is possible that the randomly overlapping nanosheets have voids present between the layers. The voids are formed between the randomly overlapping nanosheets and are generally brought about as the nanosheets are effectively monolayers of material which due to the high anisotropy of the layer may not be 100% flat and form wrinkles, sheet bending and overlapping sheets, giving rise to textural pores.

It should also be borne in mind that the active material described herein is a material that transitions from the structural intercalation of water at low humidity (leading to layer expansion, but only in one dimension, with all other structural features remaining intact) to the swelling and possibly exfoliation of the interlayer space by several layers of water at high relative humidity, which may ultimately lead to a "particle hydrate".

As noted above a change of at least one size dimension, and/or of the refractive index causes a change from the first optical thickness to at least a second optical thickness. This means that a change from the first optical thickness to the second optical thickness (e.g. a change of at least one size dimension, and/or of the refractive index) brings about (a) a change of colour of the device due to interference effects, and/or (b) a change in the resistance and/or in the resistivity of the active material.

The change of the first optical thickness to a second optical thickness brings about a change of structural colour of the device such that these effects can beneficially be exhibited and exploited by thin film devices.

As the colour changes with the change in optical thickness an indication is inherently provided that e.g. the humidity level of the environment has changed or that another vapour analyte (e.g. ethanol, isopropanol, ammonia, other alcohols, amines, solvent vapours or gases such as $CO_2$ or $NH_3$) or gas is present.

Alternatively or additionally the change in optical thickness is brought about e.g. by sorption of the analyte into the active material (change in chemical composition of the thin film due to sorption of analyte within or between the layers—this is because at low humidity levels one or two water molecules may be accommodated in structural pores within the nanosheet layers, whereas most of the water will be accommodated between nanosheets of layer).

The sorption of the analyte can also cause a change in ionic conductance and hence of the measured resistance of the thin film device.

The device advantageously further comprises a substrate, such as preferably one selected from the group of materials consisting of quartz, glass, plastic, polymer, metal, silicon, silicon coated with silicon oxide, transparent conducting oxides and arbitrary combinations of two or more of the aforementioned compounds. These various substrates (i) facilitate the possible detection of changes in colour of the device, (ii) ensure the integration into electric circuits by means of e.g. conductivity, (iii) provide the transparency, (iv) mechanical support for the device, or (v) a combination of one or more of these aspects.

The device can also further comprise at least one layer of a first optical contrast material having a refractive index, which is different from or equivalent to the refractive index of the active material. This enables the construction of multi-layered structures.

It is particularly preferred if multi-layered structures are built up of periodic bilayers composed of the first optical contrast material and of the active material. Such multi-layered structures are also referred to as Bragg stacks or as one-dimensional photonic crystals. The resultant bilayered structure advantageously permits further design possibilities of the device. The device can advantageously be composed of a plurality of such bilayers.

1DPCs, referred to as Bragg Stacks (BS) or Bragg mirrors, are periodic multilayer systems comprising two materials with different refractive indices (RI), which are capable of translating chemical, physical or biological environmental stimuli into an optical read-out, induced by a shift in their stop band position. Besides, these periodic structures are capable of tuning the colour they display while keeping their transparency, thus opening up the possibility to fabricate smart windows that change their colour as a function of the environmental conditions.

By means of the present invention particle/nanosheet-based "smart" 1D photonic crystals can also be developed as versatile humidity sensors with optical read-out. The ultra-high stop band shift of in excess of 500 nm using e.g. $H_3Sb_3P_2O_{14}$ nanosheets/$TiO_2$ nanoparticle-based Bragg stacks, or a switchable transparency through optical contrast loss of e.g. $H_3Sb_3P_2O_{14}$ nanosheets/$SiO_2$ nanoparticle-based Bragg stacks, are unique features of the proposed sensing platform. Such sensors act as a colour tunable "optical nose" with a high selectivity for water vapour. The unprecedented sensitivity of the photonic response towards humidity is demonstrated by an ultrafast (<3 s) shift of the Bragg peak by as much as 517 nm in this particular configuration. Large shifts in the Bragg peak can be induced by an approaching finger, thus translating into a full-spectrum colour shift under touchless conditions. By combining the nanosheets with e.g. a low refractive-index material such as $SiO_2$, the reflectivity of the 1 DPC completely vanishes upon water adsorption, resulting in fully transparent devices due to the diminished refractive index contrast. The observed ultrasensitive, fully reversible and spatially confined colour change over the entire visible spectrum near e.g. a fingertip provides a unique optical sensing principle enabling touchless tracking of finger movements based on a simple optical read-out. This second property, the gradual loss of reflectance accompanied by a colour change also makes such multilayers potential candidates for use in privacy window or smart window applications.

It is known that the porous nature of some component materials can be used to detect different organic vapours and humidity by means of RI changes upon infiltration of the multilayer system with water molecules. However, the observed shifts in the Bragg peak of these porous materials are rarely larger than a few tens of nanometers, and well below 100 nm which limits the resolution in terms of humidity sensing. In contrast to this, the present invention permits shifts in the Bragg peak of more than 100 nm and in some instances of more than 500 nm, making these kinds of devices suitable for completely new fields of application. Depending on the application, the devices may not even require electric circuits to read out the sensing results when a change in the environment is detected, as these can be indicated by a change in the colour of the device.

Previous Bragg stack-based devices having a good optical response were achieved for example by integrating active polymer layers into a Bragg stack. The panchromatic stop band shift induced by the layer swelling in the presence of liquid water however comes at the expense of a slow response time as well as low thermal, chemical and mechanical stability of the active organic layers making these materials unsuitable for such applications. These downsides are no longer present in the use of the active material in accordance with the present invention, which also allows the ultrasensitive detection of moisture, rather than only liquid water.

Preferably the optical contrast material used in the present invention is selected to act as at least one of the following:
(i) a gate ensuring the access of analyte (e.g. water molecules) present in the environment to the moisture sensitive layer(s) of the active material;
(ii) to be able to determine and tailor the optical properties of the multilayer structure and, hence, its structural colour;
(iii) to allow an optical contrast tailoring by adjusting the refractive index of the optical contrast material with respect to the active material.

The refractive index of the first optical contrast material is selected such that it is different from the refractive index of the active material either when a change of humidity has been brought about or before the change in humidity is brought about. The change in refractive index to or from an at least substantially like refractive index brings about a change in colour to transparent or vice versa. Alternatively the refractive indices never match and the change in refractive index brings about a change of colour of the device from e.g. blue to red.

The colour change from completely transparent to colour or from colour to completely transparent is observed when the refractive index of the active material and that of the first optical contrast material is selected such that these at least substantially coincide at a selected humidity level of the environment.

Advantageously the first optical contrast material is selected from the group of materials consisting of dielectric materials, polymers, sol-gel materials, nanoparticles, framework materials in nanoparticulate form or as a uniform thin film or nanosheets and arbitrary combinations of two or more of the aforementioned materials.

The nanoparticles are preferably $TiO_2$, $SiO_2$, $ZrO_2$, $SnO_2$ nanoparticles or framework material nanoparticles, the framework materials are preferably zeolites or metal-organic frameworks or porous polymers in a nanoparticle form but also in the form of a continuous thin film. The nanosheets are preferably selected in accordance with the type of active material used in the device, but can also include MOF nanosheets, layered double hydroxides (LDH), layered oxides, layered transition metal dichalcogenides or clays.

In accordance with a particular preferred embodiment of the present invention the device comprises a stack, wherein the stack is preferably composed of at least one, preferably of at least two bilayers, wherein each bilayer is formed by one layer of the first optical contrast material and one layer of the active material.

Advantageously the stack of bilayers of alternating layers forms a one-dimensional photonic crystal, i.e. a so-called Bragg stack or Bragg mirror or dielectric mirror. Moreover, it is preferred that 1 to 30 first bilayers, in particular 3 to 10, of such first bilayers are provided on top of one another to form a stack of first bilayers, wherein a first bilayer is defined as one layer of the first optical contrast material and a layer of the active material arranged such that either the active material is on the top or the first optical contrast material is on the top.

It is particularly preferred if the different layers of the first bilayers repeat continuously, however, applications may exist in which one departs from this concept. In this connection it should be noted that it is optionally possible to incorporate at least one further layer of active material in a stack of bilayers. This further layer is then a defect and can be included as a bottom layer (bottom defect), a top layer (top defect) or as a layer within the stack, preferably at the middle of the stack, as a resonator (or cavity) structure.

Preferably each layer of the active material of the bilayer of a Bragg stack has a thickness selected in the range from 5 nm to 2000 nm preferably 30 nm to 1000 nm. These thicknesses are measured in vacuum for dry conditions at 0% relative humidity, this means in a state where the active material has a minimum layer thickness.

Likewise each layer of the first optical contrast material has a thickness selected in the range of from 5 nm to 2000 nm, preferably 30 nm to 1000 nm. The thickness of these layers can also be determined by AFM, ellipsometry or by scanning electron microscopy (SEM).

Preferably the thickness of a layer of the active material of a first bilayer is at least substantially the same as the thickness of the further layers of the active material in a stack of first bilayers. The thickness of a layer of the optical contrast material of a bilayer is at least substantially the same as the thickness of the further layers of the optical contrast material in a stack of bilayers. This means that each bilayer preferably has substantially the same thickness as any other bilayer in the stack and, therefore, the multilayer stack is periodic.

The stack of bilayers preferably has a thickness selected in the range of from 10 nm to 120000 nm, preferably in the range of from 300 nm to 12000 nm and depends on the number of bilayers, as well as the respective layer thicknesses of the active material respectively of the optical contrast material. A typical number of bilayers in a stack then correspond to a stack of e.g. 5 bilayers. These device thicknesses are given for the material of the Bragg stack (bilayers) and do not include the thickness of the supporting substrate. The thickness of the supporting substrate is preferably selected in accordance with the desired application and can range e.g. from 200 nm to 20 mm, preferably from 2 μm to 10 mm.

Such devices can advantageously be used for applications in the UV, the visible and the IR spectral range.

In a further preferred embodiment of the present invention the device experiences a change in colour and this can be selected from the group consisting of the change in colour from a colour to transparent, from transparent to a colour, from transparent to transparent or from a first colour to a second colour, such as from blue to red, with the spectral change from a first colour to a second colour being associated with a change of the position of the optical stop band measured in reflectance or transmittance of at least 1 μm.

The colour change is caused by the change in the optical thickness of the individual layers in the presence of analyte molecules (in the more preferred embodiments these are water molecules).

In this connection it should be noted that the change from transparent to transparent might be a change from UV reflective to IR reflective, UV reflective to transparent in the visible or vice versa, from IR reflective to transparent in the visible or vice versa. In this context it should also be noted that UV reflective means that the optical band gap is placed in the UV spectral range and the Bragg stack is transparent to visible light, IR reflective means that the optical band gap is placed in the IR spectral range and the Bragg stack is transparent in the visible spectral range, transparent in the visible means that the refractive index of the active material and that of the optical contrast material is (substantially) the same.

Preferably the device further comprises at least one layer of a second optical contrast material being different from the at least one layer of a first optical contrast material and having an at least substantially different refractive index as the first optical contrast material, wherein the first optical contrast material, the second optical contrast material and the active material are laminated so as to form a stack, in which the first and second optical contrast material form a bilayer, on the top of which ("top defect") or below which ("bottom defect") only one layer of the active material exhibiting a different optical thickness from the layers in the stack is deposited as a defect structure, or wherein a layer of active material is incorporated into a stack composed of at least one, preferably of at least two, bilayer(s), with at least one and preferably all of the at least one bilayers being formed by one layer of the first optical contrast material and one layer of the second optical contrast material, wherein the layer of active material is incorporated within the stack as a defect. In the last mentioned embodiment, the layer of the active material is incorporated in the stack, preferably into the middle of the stack, to form a "resonator structure".

In this connection it should be noted that the second optical contrast material is selected from the same group of materials as the first optical contrast material, the difference is that it is selected such that it is different (and, hence, its optical properties) from the first optical contrast material for the specific case of application.

Likewise the same layer thicknesses as for the first optical contrast material apply for the second optical contrast material.

In this connection it should be noted that the difference between the refractive index of the second optical contrast material and the refractive index of the first optical contrast material amounts to a difference of at least 5% preferably of at least 10%.

Particularly preferably 1 to 30 second bilayers and in particular 3 to 10 of such second bilayers form a stack and are provided on top of one another. It should be mentioned that the number of bilayers below and above the defect layer is substantially the same, forming a symmetric structure.

These structures are also called photonic defect structures or photonic resonators or cavity structures. The multi-layered structure including two optical contrast materials is typically non active, the defect layer is made from the active material. Advantageously this defect layer acts like a "dopant" and localizes light in the band gap, creating an allowed wavelength range within the optical band gap.

The changes in the defect layer brought about by a change in the environment beneficially cause a change of the allowed wavelength range by at least 1 μm. The multi-layered structure includes the active material and at least one layer of an optical contrast material. Optionally the structure can also include two or more layers of the optical contrast material with each layer of the optical contrast material being formed from a different optical contrast material, these different layers can have the already specified thickness. Moreover, these stacked assemblies can include 2 to 30, more preferably 3 to 10 bilayers, in addition to the defect layer. Naturally speaking this defect or resonator structure can optionally be placed on top of a substrate as discussed in the foregoing.

This structure can also be composed of the stimuli-responsive layer material and one optical contrast material where the defect is formed by either the stimuli-responsive material or the optical contrast material.

Preferably the device described herein is selected from the group consisting of a humidity level sensor, a humidity level indicator, a resistive or optical touchless or touch positioning interface, a touchless or touch visualization platform, a breath control or analyzer platform, a smart privacy window changing colour with changing environmental conditions and a visualization platform for humid objects or the degree of humidity.

In a further aspect of the present invention this relates to a nanosheet of active material having the general formula:

$$H_a(M1)_x(M2)_yO_z \cdot nH_2O, \quad (1)$$

where M1 is selected from the group comprising group 2 elements, group 4 elements, group 5 elements, group 14 elements, group 15 elements, rare earth elements, as well as Mn, Fe, Co, Ni, Zn, Cd and all solid solution and substitution compounds of these elements; M2 is selected from the group of elements comprising group 15 elements, group 5 elements and all solid solutions of these elements, with M2 being different from M1, where a=0-10, preferably a=1 to 5; x=0-10, preferably x=1 to 5, in particular x=1 to 3; y=0-10, preferably y=1 to 10, in particular y=1 to 5, z=1-30, preferably z=1 to 25, in particular z=1 to 10 and n=0-50, wherein when x=0, y is not equal to 0, and when y=0, x is not equal to 0, with the nanosheet having an average thickness of 0.3 to 10 nm, an average width of greater than 20 nm and an average length of greater than 20 nm.

In contrast to materials such as ZnO that can be used in sensing devices the material in accordance with the present invention can be produced in the form of atomically or molecularly thin nanosheets. Nanosheets are composed of materials that for a certain thickness (height e.g. 2 nm) can have a minimum length (e.g. 20 nm) and a minimum width (e.g. 20 nm). Nanosheets typically have aspect ratios of >100, more preferably of >500.

Preferably formula (1) can be specified as formula 2 below:

$$H_a(M1)_x(M2)_yO_z \cdot nH_2O, \quad (2)$$

where M1 is selected from the group comprising group 14 elements, 15 elements, Mn, Fe, Co, Ni, Zn and Cd; M2 is selected from group 15 elements and Vanadium; a=1-5; x=1-5; y=1-10; z=1-25 and n=0-40.

More preferably formula (2) can be specified as formula (3) below:

$$H_{(6-y)x}(M1)_x^{y+}(M2)_2O_{3x+5} \cdot nH_2O \quad (3)$$

where x=1, 2, 3, 5; y=dependent on the oxidation state of M1 (indicated by $^{+y}$), typically 4-5; M1=As, Sb, Nb, Ta, Ge, Sn, Ti, Zr, Mo, Hf; and M2=P, As, Sb, V and n=0-30

In the most preferred cases of applications the active material is based on nanosheets selected from the group comprising: $H_xSb_xP_2O_{5+3x} \cdot nH_2O$, $H_2SnP_2O_8 \cdot nH_2O$, $H_2ZrP_2O_8 \cdot nH_2O$, $HTaP_2O_8 \cdot nH_2O$, $HAsP_2O_8 \cdot nH_2O$, and $H_3Sb_3As_2O_{14}$, $HSb_{1-y}Ta_yP_2O_8 \cdot nH_2O$, $H_3Sb_{3-z}Ta_zP_2O_{14} \cdot nH_2O$ where x=1, 3, y between 0 and 1, z between 0 and 2 and n=1-20.

In this connection it should be noted that the active material described in connection with this aspect can also be used in a device in accordance with the present invention described in the foregoing.

In a further aspect of the present invention this relates to the use of a nanosheet of active material in accordance with the teaching presented herein in a humidity level sensor, a humidity level indicator, a resistive touchless positioning interface, a resistive touch positioning interface, an optical touchless positioning interface, an optical touch positioning interface, a breath control or analyzer platform, a smart privacy window changing the colours with changing environmental conditions, and a touchless visualization platform for humid objects or the degree of humidity.

Figure 2:
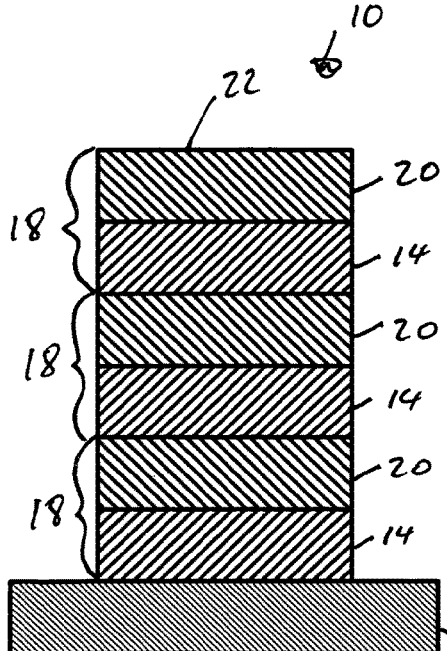
Figure 3:
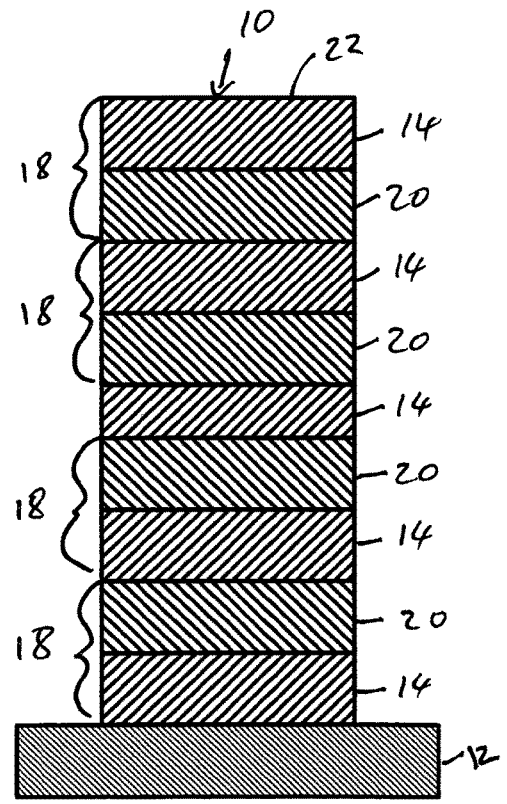
Figure 4:
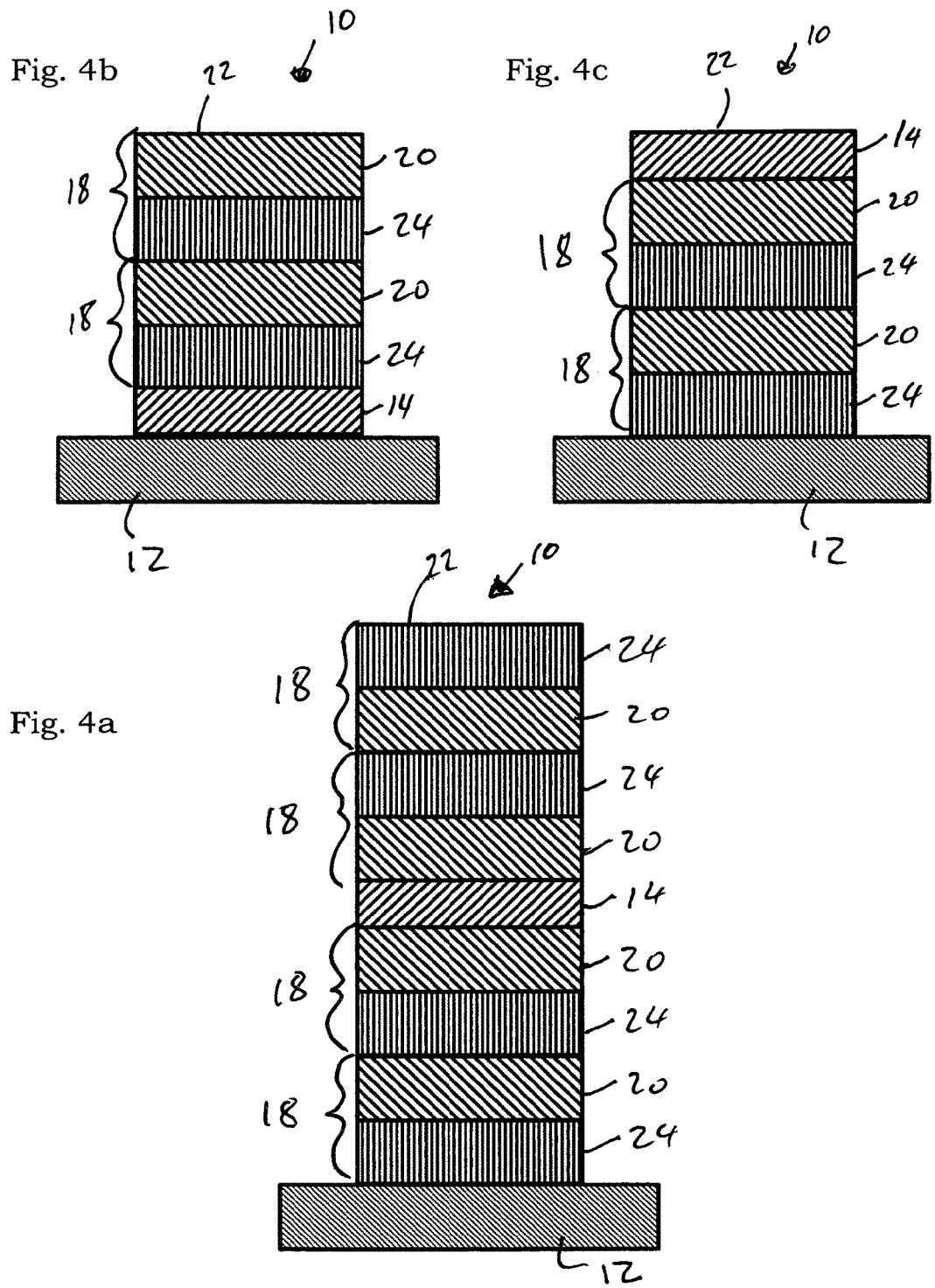
Figure 5:
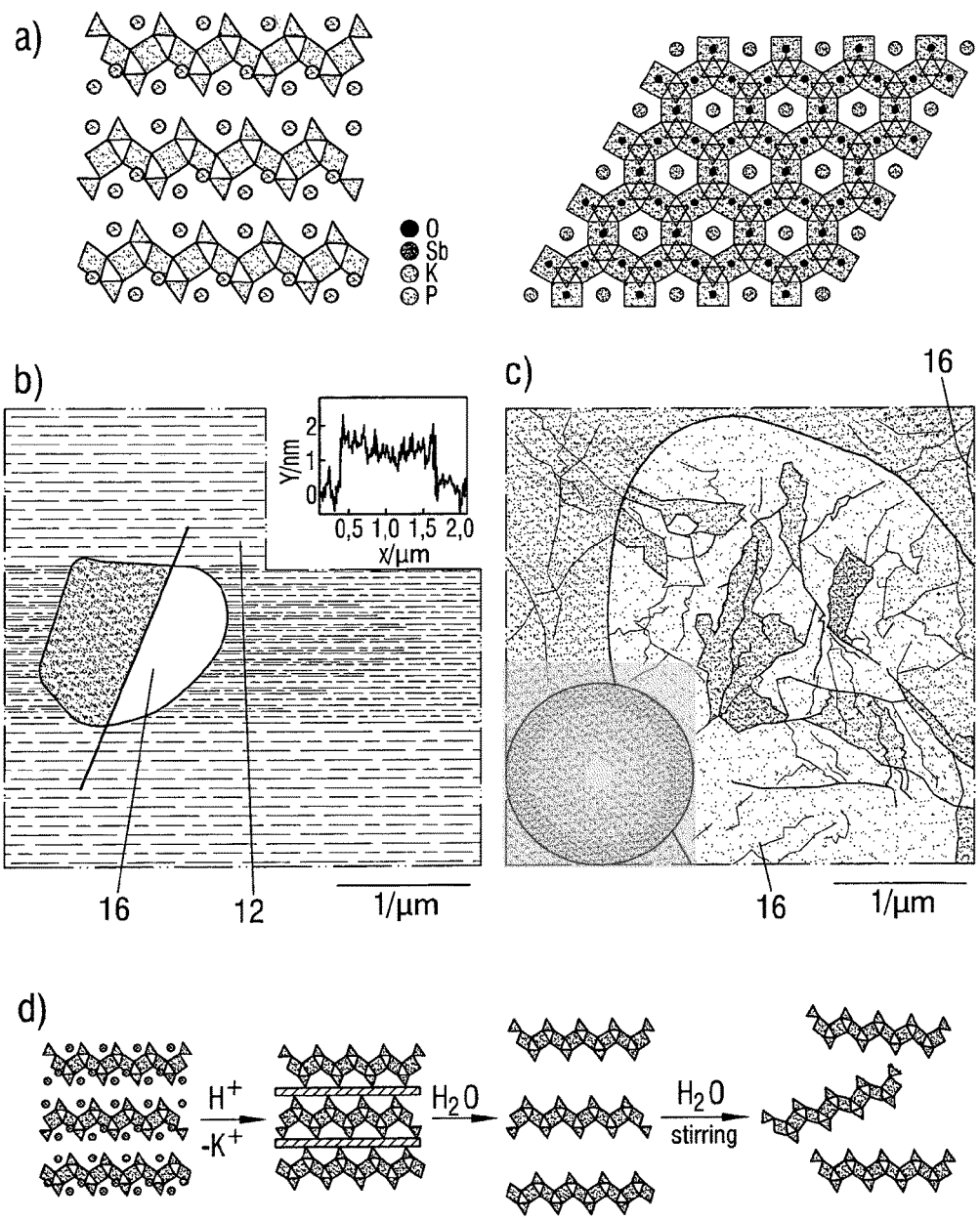
Figure 8:
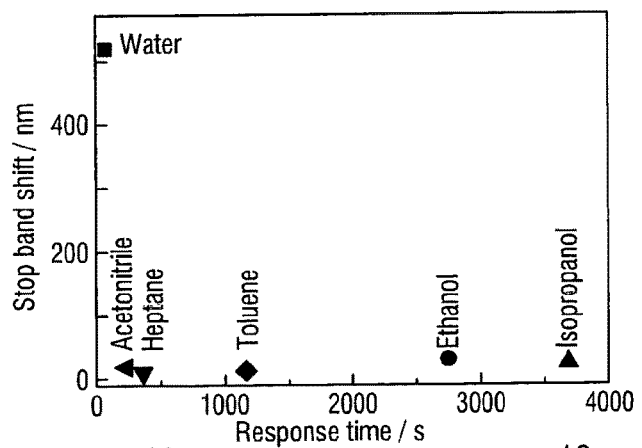
Figure 9:
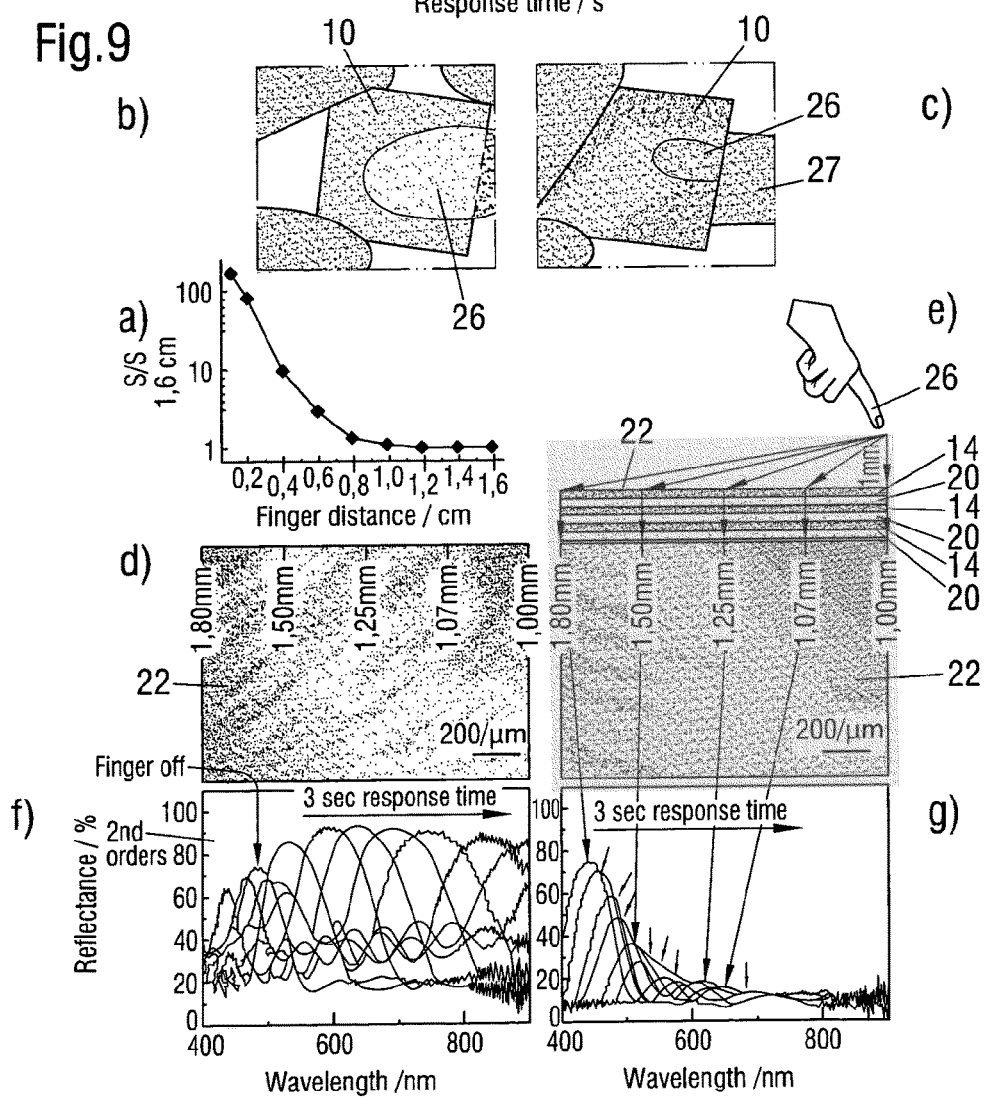
Figure 10:
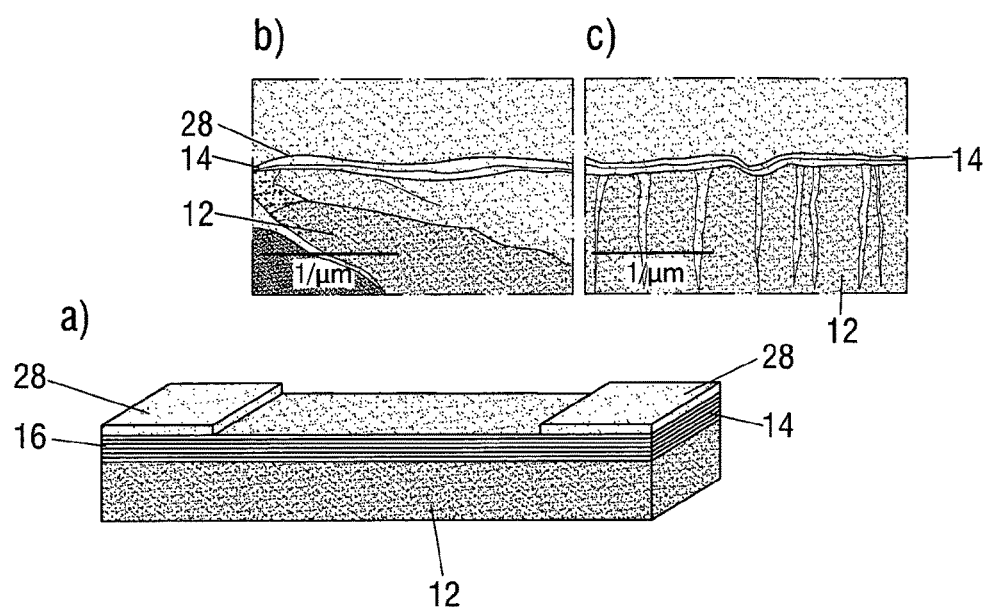

The invention will be described in the following in more detail by means of embodiments with reference to the drawings. In these there is shown:

FIG. 1 a device in accordance with a first embodiment of the present invention,

FIG. 2 a device in accordance with a second embodiment of the present invention, FIG. 3 a device in accordance with a third embodiment of the present invention, FIG. 4a to c further devices in accordance with the present invention showing a defect structure, FIG. 5 a structure model, exfoliation scheme and nanosheet characterization of an active material in accordance with the present invention, FIG. 6 conductance-based humidity sensing and cycling behavior of a device in accordance with the present invention, FIG. 7 optical humidity sensing features of the $SiO_2/H_3Sb_3P_2O_{14}$ and $TiO_2/H_3Sb_3P_2O_{14}$ Bragg stacks, FIG. 8 selectivity features of the $TiO_2/H_3Sb_3P_2O_{14}$ Bragg stack, FIG. 9 $H_3Sb_3P_2O_{14}$ nanosheet-based optical devices acting as a touchless positioning interface (TPI), FIG. 10 a) transparent thin film device with quartz substrate, spin-coated thin film and sputtered gold contacts on the top. b) SEM cross-section of the region with gold contacts on the top (bottom to top: quartz substrate, thin layer of the nanosheets, Au contacts vacuum). c) Cross-section of the thin film region without the gold contacts. Nanosheet film appears thicker due to charging effects in c.

FIG. 1 shows schematic view of a first type of device 10 in accordance with the present invention. This first device 10 is composed of a substrate 12 of glass. A layer 14 of an active material is deposited on the glass substrate 12. The layer 14 of active material is composed of a plurality of nanosheets 16. The nanosheets 16 are each formed from phosphatoantimonic acid ($H_3Sb_3P_2O_{14}$).

Depending on the specific type of active material selected, each of the nanosheets 16 has an average thickness in the range of 0.3 to 10 nm such that the layer 14 of the active material that includes a plurality of nanosheets 16 can have a thickness that is selected in the range of approximately 10 to 2000 nm. The layer 14 of the active material is hence typically composed of at least two nanosheets 16 of the active material. The nanosheets 16 can be formed on top of one another to form the layer 14 of active material by a spin coating process or by a dip coating process for example. After formation of the different nanosheets 16 on top of one another, the nanosheets 16 randomly overlap one another.

The layer of active material has a first optical thickness, defined as the thickness of the layer 14 of active material multiplied by the refractive index of the active material. The active material is selected such that it experiences a change of at least one size dimension, i.e. its thickness, of its resistance, of the refractive index or combinations of two or more of the foregoing, i.e. of the first optical thickness to a second optical thickness and optionally also of its resistivity, when the active material is subjected to a change in environment. A change in environment is usually brought about by a change in humidity, a change in the amount of a gas or vapour present in the environment.

Devices 10 existing of only one layer 14 of active material are typically referred to as thin film devices. Such thin film devices can be implemented in a humidity level sensor, a humidity level indicator, a resistive or optical touchless positioning interface (designed as a thin film interference device), a visualization platform, and a breath control or analyzer platform.

FIG. 2 shows a further schematic view of a second type of device 10. In this example of the device 10 three bilayers 18 are provided on top the substrate 12. Each bilayer 18 is composed of one layer 14 of active material and of one layer 20 of an optical contrast material. For reasons of clarity the individual nanosheets 16 of active material have been omitted from this drawing (the same is true in connection with the drawings depicted in FIGS. 3 and 4). However, it is to be understood that a layer 14 of active material is generally composed of at least two nanosheets 16. The three bilayers 18 shown in FIG. 2 form a stack 22.

The stack 22 forms a one-dimensional photonic crystal, i.e. a so-called Bragg stack or Bragg mirror or dielectric mirror. In this connection it should be noted that although the layer 14 of active material of each bilayer 18 can have a different thickness than the layer 20 of optical contrast material, each bilayer 18 at least substantially has the same bilayer thickness and each layer 14 of active material of a stack 22 at least substantially has the same layer thickness as the other layers 14 of active material of the same stack 22. The same is true for the layers of an optical contrast material 20 of each stack 22.

On forming a device 10 in accordance with FIG. 2 different options exist with regard to the selection of the basic refractive index of the layer 14 of active material and of the layer 20 of optical contrast material.

A first design option is to select the refractive index such that it is substantially the same for both materials at a given boundary condition of the environment. This given boundary condition can be a level of humidity or a gas or vapour concentration of the environment. When the level of humidity of the environment changes this leads to a change in the refractive index of the layers 14 of active material of the stack 22 and may also lead to a change in optical thickness of the optical contrast material 20. This leads to an optical contrast between the two layers 14, 20 and leads to a detectable colour (the sensing signal). Such Bragg stacks 22 exhibit colour changes from transparent to colour or transparent (like refractive indices) to transparent (different refractive indexes, however, the stop band is in the infrared or UV range).

A second design option is to provide an optical contrast material that has a refractive index different from that of the active material. Thereby an optical band gap is formed. The optical band gap shifts on an increase e.g. as the level of humidity of the environment increases or decreases. Depending on the selection of materials of the layers 14, 20 of active material and of the optical contrast material, the refractive indices can become like, i.e. the material experiences a colour change from colour to transparent. Alternatively the refractive indices remain different and at least one of the changes the Bragg stack 22 experiences is from colour to colour, e.g. from blue to red.

Regardless of whether the first or the second design option is selected, it is true that the layer thickness increases, this also leads to an optical shift in the band gap.

In this connection it should thus be noted that the change in layer thickness thus initially does not have any influence on the transparency of the structure; however, can contribute to the shift in colour from e.g. blue to red and can also contribute to the sensing signal.

FIG. 3 shows a further schematic view of a third type of device 10. In this example a defect stack 22 is formed comprising four bilayers 18 each composed of a layer 20 of a first optical contrast material and of a layer 14 of active material, with the central most layer of the defect stack 22 being composed of a further layer 14 of active material. This further layer 14 of the active material is included as a resonator structure at the middle of the stack 22. Embodiments exist (not shown) in which the further layer 14 of the active material is included as a bottom layer (bottom defect) or as a top layer (top defect) in a stack of bilayers 18.

A device 10 as shown in FIG. 3 is known as a "defect" Bragg stack or a resonator structure. This is because the one layer 14 of active material is formed within the multilayer structure, hence disrupting its periodicity. Alternatively the one layer 14 of active material could also be formed on top of the multi-layered structure to form a so called "top defect", or below the multi-layered structure to form a so-called "bottom defect".

The defect layer acts like a "dopant" and localizes light in the band gap, creating an allowed wavelength range (a dip in the reflection spectrum) within the optical band gap, the changes of the layer 14 of active material—brought about due to a change in environment—lead to a change in the defect layer which leads to a change of the allowed wavelength range by at least 1 pm.

FIGS. 4a to 4c show further devices 10 in accordance with the present invention having a defect structure. The bilayers 18 of the devices 10 shown in FIGS. 4a to 4c are each composed of a layer 20 of a first optical contrast material and of a layer 24 of a second optical contrast material. In each case the defect structure or defect layer is a layer 14 of active material. This is either applied at the middle of the stack 22 as a resonator structure (see FIG. 4a), at the bottom of the stack (see FIG. 4b) as a bottom defect or at the top (see FIG. 4c) of the stack 22 as a top defect.

Devices 10 in accordance with FIGS. 2 to 4 including at least one bilayer 18 are typically used as a humidity level sensor, a humidity level indicator, an optical touchless positioning interface, a breath control or analyzer platform, a smart privacy window changing the colours with changing environmental conditions, or as a visualization platform for humid objects or for the degree of humidity.

Due to its remarkable swelling characteristics driven by moisture and the resulting humidity-dependent proton conductivity, phosphatoantimonic acid $H_3Sb_3P_2O_{14}$ is a promising candidate for TPI based on local humidity sensing. The integration of 2D nanosheets into resistive sensing devices has been shown to give rise to a superior sensing performance as compared to the corresponding bulk material and other nanomorphologies. In a recent work, $VS_2$ nanosheets were used for resistive TPI. However, these $VS_2$ nanosheets sensors have certain drawbacks such as low chemical stability under ambient conditions (oxidation from V(IV) to V(V) and hydrolysis), and rather poor sensitivity.

By means of the devices 10 shown in FIGS. 1 to 4 a significantly enhanced response to the local humidity sheath of an approaching finger 26 (see FIG. 9) can be detected, which is superior to existing devices due to (i) the smoother (i.e. less step-wise) RH-dependent swelling behavior and conductance of the phosphatoantimonic nanosheets as compared to the bulk material, and (ii) the realization of mechanically stable thin films enabling the fabrication of ultrasensitive, low-cost resistive as well as optical TPI based on nanostructured 1D photonic crystals (1DPCs).

Thin films of phosphatoantimonic acid nanosheets and hybrid 1DPCs made thereof form chemically stable, transparent and low-cost humidity sensing devices operating with resistive and optical read-out, both of which can be applied as touchless positioning interfaces. The experimental realization of this new concept of an optical TPI, which is capable of finger movement tracking, is realized by a combination of unique features such as ultra-large stop band shift (>500 nm) and a switch from high reflectivity to complete transparency caused by the diminution of the RI contrast of the layers, as well as fast response time (<3 s), high reproducibility and stability.

The method of manufacture of devices 10 in accordance with FIGS. 1 to 4 is as follows:
a) provision of a substrate 12,
b) provision of an active material,
either c1a) depositing nanosheets 16 of said active material onto said substrate 12 to form a layer 14 of active material 16 composed of randomly overlapping nanosheets 16,
  c1a) optionally depositing a layer 20 of a first optical contrast material on said layer 14 of active material to form a bilayer 18, alternatively
  c1b) optionally depositing a layer 20 of a first optical contrast material on said substrate 12 and then depositing nanosheets 16 of said active material to form the layer 14 of active material on said layer 20 of optical contrast material to form a first bilayer 18, optionally repeating steps c1a) or c1b) a plurality of times to form a stack of first bilayers
or c2) depositing nanosheets 16 of said active material onto said substrate 12 to form a layer 14 of active material,
  c2a) optionally depositing a first layer 20 of an optical contrast material on said layer of active material 16, then depositing a layer 24 of a second optical contrast material onto said first layer 20 of an optical contrast material to form a second bilayer 18 repeating steps c2a) a plurality of times to form a stack of second bilayers 18 on said layer 14 of active material and to thereby form a so-called "bottom defect",
  c2b) optionally depositing a first layer 20 of an optical contrast material on said substrate 12, then depositing a layer 24 of a second optical contrast material onto said first layer 20 of an optical contrast material to form a second bilayer, optionally repeating steps c2b) a plurality of times to form a stack 22 of second bilayers 18 on said substrate 12, and then depositing a layer 14 of nanosheets 16 of said active material on said stack 22 to form a so-called "top defect",
  c2c) optionally depositing at least one second bilayer 18, preferably 3 to 10 such second bilayers 18 on said substrate 12, then depositing nanosheets 16 of active material to form a layer 14 of active material on said second bilayers 18, then depositing at least one further second bilayer 18, preferably 3 to 10 such second bilayers 18 on said layer 14 of active material to form a so-called "resonator structure",
d) optionally depositing electric contacts, such as gold contacts 28 (see FIG. 10), on said substrate 12 or on top of device 10, and
e) optionally removing the substrate 12 from the device 10.

The step of deposition is preferably carried out using a spin coating process. Such a process will be described in the following in detail.

The step of removing the substrate 12 from the device 10 is preferably carried out using either an etching step using e.g. acid or acetone, or a mechanical step by means of cutting away or breaking away the substrate 12 from the device 10 or peeling off the device 10 from the substrate 12 with or without the use of a swelling agent or chemical etchant.

FIG. 5 shows a structure model, an exfoliation scheme and nanosheet characterization. In particular FIG. 5a from left to right shows the structure of $K_3Sb_3P_2O_{14} \cdot 1.3H_2O$ viewed along [010] (left) and [001] (right). For a better overview only one layer is shown along [001] and for $K_3Sb_3P_2O_{14} \cdot 1.3H_2O$ the O positions between the layers have been left out. FIG. 5b shows an AFM (Atomic Force Microscope) image of an isolated $Sb_3P_2O_{14}^{3-}$ nanosheet and a corresponding height profile. FIG. 5c shows a TEM (Transmission Electron Microscope) image of overlapping exfoliated $Sb_3P_2O_{14}^{3-}$ nanosheets with a representative SAD pattern of the sample, which in the present case is the pattern resulting from two nanosheets 16 rotated against one another. FIG. 5d shows a schematic process of an ion exchange and exfoliation for $K_3Sb_3P_2O_{14}$, assuming that the swelling takes place first, followed by the exfoliation.

The layered phosphatoantimonate $K_3Sb_3P_2O_{14}$ and the proton exchanged phosphatoantimonic acid $H_3Sb_3P_2O_{14}$ were synthesized by a conventional solidstate reaction starting from $KNO_3$, $Sb_2O_3$ and $NH_4H_2PO_4$, followed by ion-exchange with 8 M nitric acid. The phosphatoantimonate is built up from anionically charged $Sb_3P_2O_{14}^{3-}$ 2 D layers interleaved by charge-compensating cations (FIG. 5a). The protonation and exfoliation process in pure water is schematically shown in FIG. 5d. The thickness of the $Sb_3P_2O_{14}^{3-}$ nanosheets 16 as determined by AFM amounts to 1.3±1 nm on average (see FIG. 5b), which agrees well with the crystallographic thickness of 1.10 nm for a single layer $Sb_3P_2O_{14}^{3-}$ nanosheet 16. The TEM and corresponding SAD image (see FIG. 5c) clearly shows the thin and randomly overlapping nanosheets (FIG. 5c). TEM-EDX as well as SEM-EDX analysis confirm that the elemental composition is very close to the expected one. The d-values of the SAD pattern agree well with those of the nanosheet pellet by powder X-ray diffraction. The XRD pattern of the turbostratically disordered nanosheet pellet, which is obtained by centrifugation at 18000 rpm and dried 100° C., can be indexed on the basis of a trigonal layer group and exhibits Warren-like peak profiles of the (hk0) reflections typical of 2D materials. The nanosheet pellet from exfoliation exhibits a silk-like morpholgy in the SE and BSE images, which is again typical of delaminated 2D materials. Thus, all data obtained point to the successful delamination of the nanosheets 16 in pure water.

Thin films of restacked nanosheets 16 with thicknesses in the range of 50-150 nm can be prepared by spin-coating the aqueous suspension of exfoliated nanosheets at different spinning speeds. Upon increasing the relative humidity from 0-100%, the nanosheet film swells to almost double its thickness (e.g. from 72 nm to 128 nm). Hereby, a particularly pronounced change is observed in the high humidity range above 90% RH (112-128 nm). This effect is accompanied by a RI decrease (from 1.62 to 1.52) in the whole humidity range as determined by spectroscopic ellipsometry, with a pronounced drop in the RH range above 90%, corresponding to the water uptake and the resulting thickness change. The RI increase and the nearly unchanged layer thickness in the low humidity range up to 10% RH are rationalized by the structural pore filling of the randomly restacked nanosheets. The continuous RI decrease in the higher RH range then is the result of mixing the refractive indices of water (1.33) and the nanosheets 16.

The humidity-responsive nanosheet thin films can directly be used as a touchless positioning interface based on resistive humidity sensing. The transparent thin film device 10 for resistivity sensing is displayed in FIG. 10 along with two SEM cross section images from different areas, which illustrate the ultrathin nature of the device. The RH dependent conductance was measured in a purpose-built humidity chamber where the RH was adjusted by means of the defined vapour pressure of saturated salt solutions or with a gas flow setup mixing argon with 0% and 93.5% RH, respectively.

FIG. 6a shows the ionic conductance as a function of RH obtained from measurements above saturated salt solutions (salt adsorption & desorption) and with an argon flow setup (gas flow desorption & adsorption) for a film device spin-coated at 2000 rpm. FIG. 6b shows the cycling behavior of the same film device 10 between 0 and 47% RH.

Remarkably, an increase in ionic conductance of the sample can be observed with increasing RH by five orders of magnitude over the complete humidity range, with only a small hysteresis loop (FIG. 6a). The cycling behavior of the thin film device 10 between 0 and 47% RH shows good reversibility and well defined and reproducible response kinetics (FIG. 6b). A response time of 57 s and a fast recovery time of 11 s for 0% to 47% RH (determined as 90% of the total signal change) can be obtained. This compares well to the response kinetics reported for $VS_2$ nanosheet devices (30-40 s and 12-50 s for response and recovery time, respectively) and is rather fast compared to other nanostructured sensing devices. Note that the measured response time contains the humidity response of the thin films 14 in addition to the time to reach the saturation of the RH in the chamber. The RH dependence of the proton conductance of the nanosheet thin film device 10 is quite different from that of phosphatoantimonic acid bulk material as reported in the prior art. While the bulk material shows distinct step-like behavior, this is not the case for the thin nanosheet film device 10. The smooth increase in conductance with increasing RH is attributed to the smaller particle size, leading to an increased amount of grain boundary adsorption, and to the non-uniform interlayer space resulting in less well-defined water adsorption sites between the randomly oriented nanosheets 16. Such textural effects likely change the water uptake mechanism from that of a lattice hydrate (bulk material) to that of a particle hydrate (nanosheets), which accommodates a large amount of water molecules on the internal and external surfaces of the nanosheets.

Bragg stacks 22 were assembled from (i) $H_3Sb_3P_2O_{14}$ nanosheet thin films as the humidity-sensitive component and (ii) either $TiO_2$ or $SiO_2$ nanoparticle layers 20 providing the required RI contrast. At ambient air (30% RH), the nanosheet film shows a refractive index of 1.56 as determined by spectroscopic ellipsometry While $TiO_2$ nanoparticles exhibit a higher RI (1.84), $SiO_2$ nanoparticle layers show a lower RI (1.34). The particle nature of the $TiO_2$ and $SiO_2$ layer acts as a gate, ensuring the access of the water molecules to the moisture-sensitive nanosheet layers through textural porosity.

The morphology of the three different materials—the spherical silica colloids, the irregular shaped titania particles and the laminar nanosheets 16—can be clearly distinguished in the inset of the figures. The spectral position of the maximum of the Bragg peak and thus the structural colour at normal incidence are given by the expression (4):

$$\lambda_B = 2 \cdot (n_1 d_1 + n_2 d_2) \quad (4)$$

where $n_1$ and $n_2$ are the RIs of the different layers and $d_1$ and $d_2$ their respective thicknesses.

With this, the spin-coating technique allows the thickness of the deposited films to be fine-tuned and hence, the structural colour displayed by the Bragg stacks 22 by modifying the experimental parameters. For the fabrication procedure carried out in this work, only the spin-coating speed was varied from 2000 rpm to 4000 rpm, while the concentration of the different colloidal suspension, or any other parameter of the process, was kept constant.

In order to study the different features of optical humidity sensors, the two Bragg stacks 22 were introduced into a closed chamber with a transparent upper window, and the position of the Bragg peak was measured for different RH values controlled by saturated salt solutions at 25° C. Note that the porous nature of the nanoparticle layers and the fast equilibration time of the nanosheet layers ensure an easy access of the water molecules into the device 10 and their fast equilibration throughout the device 10.

FIG. 7a shows a scheme of the suggested humidity sensing mechanism. FIG. 7b shows experimental (solid spectra) and simulated (dashed spectra) reflectance spectra of the $SiO_2/H_3Sb_3P_2O_{14}$ Bragg stack 22 at different relative humidity values. FIG. 7c shows experimental (solid spectra) and simulated (dashed spectra) reflectance spectra of the $TiO_2/H_3Sb_3P_2O_{14}$ Bragg stack 22 at different relative humidity values.

The general sensing mechanism of the Bragg stacks 22 is schematically depicted in FIG. 7a. In the present case, the thickness of the particle layers is assumed invariable, so three main processes affect the humidity-dependent optical response of the Bragg stack 22 (according to expression (4)): (i) the change in RI of the $TiO_2$ and $SiO_2$ nanoparticle layers with the adsorption/desorption of water into their textural pores (i.e. interparticle voids), (ii) the change of the RI of the nanosheet layers through uptake/loss of water, (iii) the humidity-dependent thickness of the nanosheet layers 14. Whereas for $SiO_2$ and $TiO_2$ the effective RI of the layers increases with increasing water content due to the pore filling process, it decreases for the nanosheet layers 14 as the effective RI approaches that of pure water with increasing degree of hydration. The latter phenomenon is driven by the massive swelling of the nanosheet layers 14 with increasing RH, in contrast to the more compact nanoparticle layers. These parameters, which can be extracted from the humidity-dependent reflectance spectrum, determine the optical properties; the overall changes can also be visibly perceived as a colour change. The two Bragg stacks 22, $H_3Sb_3P_2O_{14}$/$SiO_2$ and $H_3Sb_3P_2O_{14}$/$TiO_2$, qualitatively behave very differently. In both cases, the swelling behavior of the layers 14 of nanosheets 16 defines two different response ranges: the lower RH range (up to 90%) and the high RH range (from 90% to 100%) when condensation of water takes place.

In the case of the $H_3Sb_3P_2O_{14}$/$SiO_2$ based Bragg stack 22, the photonic stop band red-shifts by 100 nm in the lower RH range. The sequence of experimentally taken spectra for different values of RH is plotted in FIG. 7b (solid lines). It has been found that for increasing values of the water vapour pressure, the Bragg peak shifts into the red, while its intensity gradually decreases and finally vanishes. The colour displayed by the sensor follows this behavior and for the highest value of humidity, the Bragg reflector switches off, i.e. becomes completely transparent. This effect finds an explanation in the elimination of the optical contrast between the layers forming the Bragg stack 22 with increasing RH. While the RI of the particle layer (the layer of optical contrast material 20) increases and its thickness roughly remains constant, two different effects take place in the layer 14 of active material: (i) the decrease of the RI, which contributes to a blue shift of the Bragg peak, is (ii) overcompensated by the increase in layer thickness, hence leading to an overall red-shift of the Bragg peak. However, since the RI of the layers 14 of active material gradually decreases, while that of the nanoparticle layers keeps increasing, both values ultimately become equal at around 90% RH, leading to the disappearance of the optical contrast. As the photonic stop band is canceled out, the optical sensor turns completely transparent in a highly reversible fashion, and light is transmitted by the structure throughout the visible range.

The specular reflectance spectra taken for the $TiO_2$/$H_3Sb_3P_2O_{14}$ BS are plotted in FIG. 7c (solid lines). The Bragg peak red shifts by 100 nm in the RH range of 0-90%. Contrary to the $SiO_2$ containing Bragg stack 22, however, the reflectance rises with increasing RH and the stop band broadens, which can be rationalized by the increase in optical contrast of the layers with increasing RH. We observe a total red-shift of more than 517 nm, shifting the Bragg peak out of the visible range into the IR, while the second order Bragg peak is observed at 495 nm (red curve of FIG. 7c). The observed red-shift at high RH is the largest ever observed for a BS for moisture sensing applications. Note that besides the unique colour changes also the ultrafast response time and the high reproducibility and cyclability of the Bragg stack device 10 is unprecedented.

Simulations of the optical spectra were carried out with a Matlab code out to confirm the optical properties observed for the Bragg stacks 22 (FIG. 7, dashed lines; for the input parameters used, see FIG. 10 and Table 1 and 2). The excellent agreement between the values obtained in both cases validates the quality of the measurements presented herein and of the sensing mechanism. Hence, the main sensing effect is caused by the nanosheet layer 14 swelling (up to 3 times its original value), whereas the changes of RI of the nanosheet films and the porous nanoparticle layers have a modest contribution to the observed effect.

One essential property required from a humidity sensor is a low level of cross-talk with other analytes, i.e. a response exclusive to e.g. water molecules. The selectivity towards water was tested by studying the sensitivity of the sensor to solvent vapours with different chemical properties and polarities (water, ethanol, toluene, isopropanol, heptane and acetonitrile) by monitoring the Bragg peak position and the time for the Bragg peak total shift (referred to as response time) with two different Bragg stacks 22 ($TiO_2$/$H_3Sb_3P_2Oi_4$ (FIG. 8) and $SiO_2$/$H_3Sb_3P_2O_{14}$).

FIG. 8 shows selectivity features of the $TiO_2$/$H_3Sb_3P_2O_{14}$ Bragg stack 22. In particular a diagram showing the optical stop band shift of the $TiO_2$/$H_3Sb_3P_2O_{14}$ Bragg stack 22 as a function of the response time of 0% and 100% relative humidity change is shown. Results of water are compared with polar and protic solvents: ethanol and isopropanol, polar and non-protic solvents: acetonitrile, and non-polar solvents: heptane and toluene.

Compared to water vapour, the apolar (heptane, 10 nm and toluene, 12 nm) and aprotic polar solvents (acetonitrile, 17 nm) only show minute shifts with fast response times (several seconds). In contrast, the protic solvents with medium polarity (ethanol, 30 nm and isopropanol, 25 nm) show somewhat larger shifts, with response times of more than 2000 s. The observed response is likely due to delayed interlayer diffusion of the protic solvents slowed down by the larger size (isopropanol>ethanol>water) and less pronounced solvation/hydrogen-bonding capability of the alcohols as compared to water. In summary, not only a significantly larger stop band shift (more than 15 fold) in response to water vapour is observed, but also considerably shorter response times (30 s) are observed, which establishes a unique selectivity of the Bragg stack 22 to water vapour.

FIG. 9a shows sensing response characteristics as a function of the finger distance of a thin film device obtained by spin-coating at 3000 rpm. The measurement was performed at around 30% RH. FIG. 9b shows a photograph of the $SiO_2$/$H_3Sb_3P_2O_{14}$ Bragg stack 22 approached by a finger 26 covered with a nitrile glove 27. No response is observed in this case. FIG. 9c shows a photograph of the $SiO_2$/$H_3Sb_3P_2O_{14}$ Bragg stack 22 approached by a finger 26. Note that the finger 26 is not in contact with the stack 22. FIG. 9d shows a real colour microscope image of the $TiO_2$/$H_3Sb_3P_2O_{14}$ Bragg stack 22, showing the lateral colour gradient around the finger position. The finger 26 was positioned at the top right corner, at a vertical distance of 1 mm from the Bragg stack surface. Real distances from the finger 26 to the corresponding image positions are indicated. FIG. 9e shows a real colour microscope image of the $SiO_2$/$H_3Sb_3P_2O_{14}$ Bragg stack 22 showing the lateral colour gradient around the finger position. The scheme shows the position of the finger 26 in the top right image corner in a vertical distance of 1 mm. The real distances from the finger 26 at the corresponding image positions (calculated by the Pythagorean theorem) are indicated. FIG. 9f shows reflectance spectra of the $TiO_2$/$H_3Sb_3P_2O_{14}$ taken after 3 s response time while the finger 26 is approaching. The different curves (depicted in gray scale) correspond to the different magnitudes of the response. FIG. 9g shows reflectance spectra of the SiO$_2$/H$_3$Sb$_3$P$_2$O$_{14}$ taken after 3 s response time while the finger 26 is approaching.

Both the conductance of the thin film and the optical properties of the Bragg stacks 22 show a reproducible and selective response to changes in RH. Therefore, these thin film devices 10 are potential candidates for touchless positioning interfaces, since the human finger 26 is surrounded by a distance-dependent humidity environment. To probe the touchless sensing capability of the thin films, first, the nanosheet film 14 on a quartz substrate 12 was studied. Hereby, an increase of the conductance by more than a factor of 170 was observed when the distance of the finger 26 from the substrate was reduced from 1.6 cm to 0.1 cm at 30% ambient RH (see FIG. 9a). This is notably higher than the value reported for VS$_2$ thin film devices, which exhibited a maximum signal change of 3 for finger-off and finger-on state. Even at larger distances of 0.8 cm a signal increase by 33% is obtained, suggesting that this type of sensor can be used in rather long-range interaction devices. By manipulating the conductance with the finger 26 in a dynamic measurement, it is obvious that the thin film device 10 has a very fast and reversible response to finger distance changes.

With the highly sensitive photonic read-out scheme presented above, the tools are at hand to go one step further and develop an optical touchless positioning interface based on the lateral tracking of "humid" objects with an optical read-out visible by the naked eye. For these BS-based optical devices 10, no integration in an electronic assembly is required to visualize the finger position above a photonic surface. The experiments presented herein demonstrate the feasibility of this touchless optical sensing principle and are summarized in FIG. 9.

Positioning the finger at a vertical distance of 1 mm from both Bragg Stack surfaces (TiO$_2$ and SiO$_2$ based) leads to a colour gradient along a distance between 1.0 mm and 1.8 mm from the fingertip, as shown in the microscope pictures corresponding to the two configurations proposed for TiO$_2$/H$_3$Sb$_3$P$_2$O$_{14}$ and SiO$_2$/H$_3$Sb$_3$P$_2$O$_{14}$ Bragg stacks 22, respectively (FIGS. 9d and 9e). This is in perfect agreement with the conductance behavior, as in the small distance range the sensing signal drops similarly fast (FIG. 9a) due to the spatially dependent humidity gradient around the human finger 26. Looking at the structural colours of the gradient, the colour at 1.0 mm real distance corresponds to the 100% sensing signal (where the optical contrast and reflectance are lost) in the case of the SiO$_2$/H$_3$Sb$_3$P$_2$O$_{14}$ Bragg stack 22.

In both cases, the structural colour for a distance of 1.5 mm corresponds to a RH of around 90% (see FIG. 7). The captured reflectance spectra (FIGS. 9f and 9g) for both Bragg stacks 22 show a maximum Bragg peak shift after 3 s similar to the measured shifts at 100% RH. The cycling behavior corresponding to the SiO$_2$/H$_3$Sb$_3$P$_2$O$_{14}$ BS demonstrates—in addition to the ultrafast response time—the high reversibility and reproducibility of the sensing event. These features were also demonstrated by lateral movement of the finger 26 across the Bragg stack 22. An instantaneous response following the finger 26 movement was observed, which is equivalent to a high-fidelity tracking of the finger movement.

It should be noted that the Bragg Stack 22 response is exclusively due to the local water vapour atmosphere surrounding the finger, rather than a temperature effect, as (i) the response in the finger-on state is completely analogous to the measurement at very high RH, and (ii) no colour change is observed if the finger 26 is protected by a nitrile glove (no water atmosphere but higher local temperature) (FIG. 9b), while a fast and pronounced colour change is directly seen by an approaching the naked finger 26 (FIG. 9c). Nevertheless, it is assumed that the body temperature plays a role by enhancing the diffusion of the water molecules, which is reflected by the shortened response times compared to the humidity sensing measurements carried out at RT.

Example Manufacture of K$_3$Sb$_3$P$_2$O$_{14}$

For the synthesis of K$_3$Sb$_3$P$_2$O$_{14}$ the precursors (KNO$_3$ (99%, Merck), Sb$_2$O$_3$ (99.6%, Alfa Aesar), NH$_4$H$_2$PO$_4$ (98%+, Acros Organics)) were thoroughly ground in a stoichiometric ratio and heated in the first step to 300° C. and after grinding in a second heating step to 1000° C. (for a period of each 24 h). For the proton exchange reaction 2 g of K$_3$Sb$_3$P$_2$O$_{14}$ were treated with 250 mL of 8 M nitric acid (diluted 65 wt %, Merck) overnight (for a period of 12 h), filtrated, washed with ethanol (99.8%, ca 15 mL) and dried at room temperature for 4 h. This treatment was repeated a second time to complete the exchange reaction. The success was monitored by XRD. Exfoliation was carried out by stirring the H$_3$Sb$_3$P$_2$O$_{14}$ vigorously overnight (16 h) in pure water with a concentration of bulk protons of 7.3 mmol L$^{-1}$. The obtained colloidal suspensions were centrifuged at 3000 rpm for 30 min to remove non-exfoliated bulk material. The supernatant is a suspension of mainly single-layer nanosheets. To obtain the nanosheet pellet, an additional centrifugation step was applied at 18000 rpm for 30 min. The supernatant was discarded and the gel-like colourless wet aggregate was dried at 100° C. for at least 4 hours.

Examples of other nanosheets that can be used in terms of the present invention are H$_2$SnP$_2$O$_8$.nH$_2$O, H$_2$ZrP$_2$O$_8$.nH$_2$O, HTaP$_2$O$_8$.nH$_2$O, HSb$_{1-y}$Ta$_y$P$_2$O$_8$.nH$_2$O, HAsP$_2$O$_8$.nH$_2$O, H$_3$Sb$_3$As$_2$O$_{14}$, where x=1, 3, 0<y<1 and n=1-20. In this respect it can be summarised that some of the materials quoted above can be produced according to known published methods of synthesis. It should however in this context be noted that the manufacture of the material per se is known, but not all of these materials have hitherto been produced in the form of 2D planar nanosheets 16 and none of these nanosheet materials has been applied in spatially resolved humidity sensors such as Bragg stacks or thin films.

For example, H$_2$SnP$_2$O$_8$.nH$_2$O, H$_2$ZrP$_2$O$_8$.nH$_2$O can be produced according to published synthesis methods. HSbP$_2$O$_8$.nH$_2$O can be synthesized in a fashion similar to H$_3$Sb$_3$P$_2$O$_{14}$.nH$_2$O and according to syntheses described in the literature. HSb$_{1-y}$Ta$_y$P$_2$O$_8$.nH$_2$O can also be produced and exfoliated with TBAOH. HTaP$_2$O$_8$.nH$_2$O, HAsP$_2$O$_8$.nH$_2$O can be synthesized according to the literature. Exfoliation can be achieved by stirring in an aqueous TBAOH solution (molar ratio bulk protons:TBAOH=1:1 and concentration of bulk protons of 7.3 mmol L$^{-1}$). TiO$_2$ nanoparticulate sols were synthesized using the following procedure: To 75 ml of 0.1 M HNO$_3$ 12.5 ml Ti(OEt)$_4$ was added dropwise under vigorous stirring at room temperature. The reaction mixture was heated to 80° C. for 8 h and afterwards sonicated for 8 h to remove agglomerates. The colloidal solution of titania nanoparticles used for spin-coating was obtained by collection of the particles by repeated centrifugation at 20000 rpm and redispersion in methanol.

In contrast to this, SiO$_2$ nanocolloids were purchased from Dupont (LUDOX TMA, Aldrich) (Product no.: 420859-1L)

In order to prepare colloidal suspensions, the dried colourless precipitate of the water exfoliated H$_3$Sb$_3$P$_2$O$_{14}$ nanosheets 16 was redispersed with a concentration of 42 mmol in a water/ethanol mixture (60 vol % ethanol) and sonicated for 2 h. The $TiO_2$ suspensions had a concentration of 2.5 wt % in methanol. The commercial colloids of $SiO_2$ were redispersed at 3 wt % in methanol.

In order to fabricate the nanosheets 16 respectively the thin films 14, 20, 24 and the Bragg Stacks 22, all sheets respectively films were made by means of spin-coating using a spin coater (WS-650S-NPP-Lite, Laurel) Technologies Corporation) and concentrations given above. Different film thicknesses were accessed by varying the spin-coating speed which allowed the fine-tuning of the optical properties. 400 µl of the colloidal suspensions were spin-coated on plasma cleaned microscope glass slides with the dimensions of 2.5 cm×2.5 cm, alternatingly for 1 min with a defined speed, and heated to 80° C. for 15 min after each layer deposition. 2000 rpm, 3000 rpm and 4000 rpm spin-coating speeds were applied (the same speed for each layer within a Bragg stack) to tune the optical properties. For conductance measurements, this redispersed $Sb_3P_2O_{14}^{3-}$ nanosheet colloid was spin-coated at 3000 rpm or 2000 rpm for 1 min with a 10000 rpm acceleration ramp on a 1.5 cm×1.5 cm plasma-cleaned quartz glass substrate. Gold contacts were sputter-coated (108auto, Cressington) with 180 s sputtering time.

In order to carry out the structural characterization TEM images and selected area electron diffraction (SAD) patterns were obtained using a Phillips CM30 ST TEM (300 kV, $LaB_6$ cathode) equipped with a Gatan CCD camera. TEM-EDX analysis was performed using a Si/Li detector (Thermo Fisher, Noran System Seven). SEM images of the nanosheet pellet as well as cross-sectional images of the Bragg stacks 22 were collected using a Vega TS 5130 MM (Tescan) equipped with Si/Li detector (Oxford). AFM measurements were obtained using a Veeco CP II system in non-contact mode. XRD patterns were collected on a powder X-ray diffractometer (Stadi P, STOE) working with Ge(111) monochromated Mo-$K_{\alpha 1}$ radiation ($\lambda$=70.926 pm) or Cu-$K_{\alpha 1}$ radiation ($\lambda$=154.051 pm) in Debye-Scherrer or transmission geometry with an image-plate detector or a point detector. Well-ground samples were either put between two Mylar® foils or filled in a glass capillary. Indexing was performed with the software DiffracPlus TOPAS v4.2 (Bruker AXS). The images of the surfaces of the Bragg stack were obtained with an optical microscope (Olympus BX51), operating in reflection mode with a 4× objective.

In order to obtain the conductance measurements, two different methods were used. In the first one the films were kept over saturated salt solutions, at around 25° C. in a closed atmosphere at least 15 min before the conductance measurements. In the second measurement an argon flow set up was used. A dry Ar flow and a water vapour saturated Ar stream were mixed in different ratios to define the humidity between 0-93.5%. The setup was calibrated using the conductance values previously measured at the RH defined by the salt solutions. The cycling was performed using the Ar stream setup. The change in conductance was monitored by impedance spectroscopy with an impedance bridge (Princeton Aplied Research, VersaSTAT MC) applying an AC voltage of 500 mV and a frequency range of 1 Hz to 1 MHz. Cycling measurements were performed with a fixed frequency of 300 Hz.

All optical spectra were measured using a fiber optic spectrometer (USB2000+, Ocean Optics) attached to a microscope (DM2500, Leica) with normal incidence and the optical spectra were always taken at the same spot (1×1 mm² in area). To obtain the optical changes with relative humidity change, the Bragg stacks 22 were kept over 2 mL of the saturated salt solutions described before at around 25° C. in a closed stainless steel chamber with a transparent glass window. At each step, 15 min atmosphere equilibration time was needed. To measure the shift of the Bragg peak with the different organic solvents a different methodology was applied. The application of other solvent vapours with a defined relative pressure was realized by connecting the inserted pipette tip with a liquid-gas flow controller (Bronkhorst) and a vapourizer (CEM) with a massflow-controlled carrier gas flow. To observe a desired relative pressure of the analyte of interest, the carrier gas nitrogen (200 mL min$^{-1}$) and the liquid solvent were dosed into the CEM (controlled evaporation and mixing, W101A-130-K, Bronkhorst High-Tech), where the thermal evaporation of the solvent took place. The CEM was heated to temperatures above the boiling point. The vapour relative pressures were calculated via the software FLUIDAT, CEM calculation, which considers the actual atmospheric pressure, the temperature and the properties of the analyte (vapour pressure, heat capacity). The spectra were measured in the visible range with an OCEAN OPTICS QP400-2-UV-BX optical fiber interfaced with a LEICA DM 2500 M microscope. The obtained data were analyzed with the SPECTRA SUITE (2008) software.

The touchless positioning interface measurements were carried out using conductance measurements. The conductance measurements were carried out by impedance spectroscopy (see above) by placing a finger 26 at different distances of 0.1-1.6 cm without touching the thin film device 10.

Optical measurements were similarly carried out; a finger 26 was used to approach the Bragg stack 22 at a distance of 1 mm. Hereby lateral optical changes were detected by the optical microscope (Olympus BX51) coupled to a CMOS camera and an Ocean Optics USB4000-XR1-ES spectrometer. A finger cycling was carried out by approaching and distancing the finger 26 in regular intervals of ca. 15 sec. To detect the stop band changes, the intensity changes at the wavelength 475 nm were followed. The optical tracking of the finger movements by the Bragg stack 22 were recorded by a conventional smart phone camera.

FIG. 10a shows a thin transparent film device 10 with quartz substrate 12, a spin-coated thin film 14 and sputtered gold contacts 28 on the top. FIG. 10b shows an SEM cross-section of the region with gold contacts 28 on the top (bottom to top:

quartz substrate 12, thin layer of the nanosheets 16 and Au contacts 28). FIG. 10c shows a cross-section of the thin film region without the gold contacts 28. In FIG. 10c the nanosheet film appears thicker due to charging effects.

Table 1 shows the refractive indices and monolayer thicknesses for the $SiO_2/H_3Sb_3P_2O_{14}$ Bragg stack measured by ellipsometry at different relative humidity values. These values were taken for the simulations at different relative humidity values (FIG. 7); n=refractive index; d=layer thickness.

| Monolayer property | 11% RH | 74% RH | 93% RH |
|---|---|---|---|
| n($H_3Sb_3P_2O_{14}$) | 1.6090 | 1.5729 | 1.5424 |
| n($SiO_2$ NP) | 1.4269 | 1.4409 | 1.4650 |
| d($H_3Sb_3P_2O_{14}$) | 52.9 nm | 70.0 nm | 83.0 nm |
| d($SiO_2$ NP) | 90.0 nm | 90.0 nm | 90.0 nm |

Table 2 shows the refractive indices and monolayer thicknesses for the $TiO_2/H_3Sb_3P_2O_{14}$ Bragg stack measured by ellipsometry at different relative humidity values. These values were taken for the simulations at different relative humidity values (FIG. 7); n=refractive index; d=layer thickness.

| Monolayer property | 11% RH | 74% RH | 93% RH |
|---|---|---|---|
| n($H_3Sb_3P_2O_{14}$) | 1.6090 | 1.5729 | 1.5424 |
| n($TiO_2$ NP) | 1.7500 | 1.7702 | 1.8000 |
| d($H_3Sb_3P_2O_{14}$) | 51.0 nm | 67.5 nm | 80.0 nm |
| d($TiO_2$ NP) | 80.0 nm | 80.0 nm | 80.0 nm |

REFERENCE NUMERALS 10 device
12 substrate
14 layer of active material
16 nanosheet
18 bilayer
20 layer of a first optical contrast material
22 stack
24 layer of a second optical contrast material
26 finger
27 glove
28 contact

The invention claimed is:

1. A device, comprising at least one layer of an active material having a first optical thickness, the active material being selected so as to experience a change (i) of at least one size dimension, (ii) of the resistance, (iii) of the refractive index or (iv) combinations of two or more of the foregoing, when the active material is subjected to a change in environment, wherein at least one layer of the active material is composed of at least two nanosheets of the active material, with the at least two nanosheets overlapping one another, wherein the active material of at least one layer has the general formula:

H$a$(M1)$x$(M2)$y$O$z$.$n$H2O, where M1 is selected from the group comprising group 2 elements, group 4 elements, group 5 elements, group 14 elements, group 15 elements, rare earth elements, as well as Mn, Fe, Co, Ni, Zn, Cd and all solid solution and substitution compounds of these elements; M2 is selected from the group of elements comprising group 15 elements, group 5 elements and all solid solutions of these elements, with M2 being different from M1; where a=0-10; x=0-10; y=0-10; z=1-30; and n=0-50, wherein when x=0, y is not equal to 0, and when y=0, x is not equal to 0.

2. The device in accordance with claim 1, wherein all layers of the active material are composed of at least two nanosheets of the active material.

3. The device in accordance with claim 1, wherein the change in environment is at least one of a change in humidity of the environment and a change of the amount of a compound present in the environment.

4. The device in accordance with claim 1, wherein the active material has an aspect ratio of length to width to height of the nanosheets of at least 20:20:1.

5. The device in accordance with claim 1, wherein the active material of all of the layers has the general formula:

H$a$(M1)$x$(M2)$y$O$z$.$n$H2O.

6. The device in accordance with claim 1, wherein at least one of the at least two nanosheets has an average sheet thickness of 0.5 to 10 nm.

7. The device in accordance with claim 6, wherein all of the at least two nanosheets has an average sheet thickness of 0.5 to 10 nm.

8. The device in accordance with claim 1, wherein at least one layer of the active material has an average layer thickness selected in the range of from 4 nm to 5 mm.

9. The device in accordance with claim 8, wherein all layers of the active material have an average layer thickness selected in the range of from 4 nm to 5 mm.

10. The device in accordance with claim 1, wherein the change of a size dimension and/or of the refractive index brings about (a) a change of colour of the device due to interference effects, and/or (b) a change in the resistance and/or of the resistivity of the active material.

11. The device in accordance with claim 1, further comprising a substrate.

12. The device in accordance with claim 11 wherein the substrate is selected from the group of materials consisting of selected from the group of materials consisting of quartz, glass, plastic, polymer, metal, silicon, silicon coated with silicon oxide, transparent conducting oxides and arbitrary combinations of two or more of the aforementioned compounds.

13. The device in accordance with claim 11, wherein a thickness of the substrate is selected in the range of from 200 nm to 20 mm.

14. The device in accordance with claim 1, further comprising at least one layer of a first optical contrast material having a refractive index, which is different from or equivalent to the refractive index of the active material at the first optical thickness.

15. The device in accordance with claim 14, wherein the device comprises a stack, wherein the stack is composed of at least one bilayer, wherein each bilayer is formed by one layer of the first optical contrast material and of one layer of the active material.

16. The device in accordance with claim 15, wherein each stack comprises 2 to 30 first bilayers.

17. The device in accordance with claim 15, wherein at least one further layer of the active material is incorporated in the stack as a defect structure, either as a bottom layer, a top layer or as a layer within the stack.

18. The device in accordance with claim 14, wherein the first optical contrast material is composed of a material being selected from the group consisting of dielectric materials, polymers, sol-gel materials, nanoparticles, framework materials or nanosheets and arbitrary combinations of two or more of the aforementioned materials.

19. The device in accordance with claim 1, wherein the change in colour is from a colour to transparent, from transparent to a colour, from transparent to transparent or from a first colour to a second colour, such as from blue to red, with the spectral change from a first colour to a second colour in particular being associated with a change of the position of the optical stop band measured in reflectance or transmittance of at least 1 pm.

20. The device in accordance with claim 14, further comprising at least one layer of a second optical contrast material being different from the at least one layer of first optical contrast material and having a refractive index different from that of the first optical contrast material, wherein the first optical contrast material, the second optical contrast material and the active material are laminated on top of one another so as to form a stack, in which the first and second optical contrast material form a bilayer, on the top of which or below which only one layer of the active material, exhibiting a different optical thickness from the layers in the stack, is deposited as a defect structure; or wherein a laminate comprising a layer of active material incorporated into a stack composed of at least one bilayer, with at least one bilayer being formed by one layer of the first optical contrast material and one layer of the second optical contrast material.

21. The device in accordance with claim 1, wherein the device is selected from the group of members consisting of a humidity level sensor, a humidity level indicator, a resistive or optical touchless positioning interface, a touchless visualization platform, a breath control or analyzer platform, a smart privacy window changing colour with changing environmental conditions and a visualization platform for humid objects or the degree of humidity.

22. A nanosheet of active material having the general formula:

$$H_a(M1)_x(M2)_yO_z \cdot nH_2O,$$

where M1 is selected from the group comprising group 2 elements, group 4 elements, group 5 elements, group 14 elements, group 15 elements, rare earth elements, as well as Mn, Fe, Co, Ni, Zn, Cd and all solid solution and substitution compounds of these elements; M2 is selected from the group of elements comprising group 15 elements, group 5 elements and all solid solutions of these elements, with M2 being different from M1; where a=0-10; x=0-10; y=0-10; z=1-30; and n=0-50, wherein when x=0, y is not equal to 0, and when y=0, x is not equal to 0, with the nanosheet having an average thickness of 0.3 to 10 nm, an average width of greater than 20 nm and an average length of greater than 20 nm.

* * * * *